US009291606B2

(12) United States Patent
Hansteen et al.

(10) Patent No.: US 9,291,606 B2
(45) Date of Patent: Mar. 22, 2016

(54) QUALITY CONTROL DEVICES AND METHODS FOR RADIOPHARMACEUTICALS

(75) Inventors: Ole Henrik Hansteen, Oslo (NO); Jan Borge Jakobsen, Asker (NO); Svein-Erik Lindgaard, Oslo (NO); Xavier Franci, Loncin (BE); Line Roed, Oslo (NO); Arnfinn Andersen, Oslo (NO); Gro Johansen, Oslo (NO); Torsten Knuttel, Oslo (NO); Karina Martha Langseth, Oslo (NO)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 0 days.

(21) Appl. No.: 13/817,864

(22) PCT Filed: Aug. 22, 2011

(86) PCT No.: PCT/US2011/048564
§ 371 (c)(1),
(2), (4) Date: Aug. 30, 2013

(87) PCT Pub. No.: WO2012/024663
PCT Pub. Date: Feb. 23, 2012

(65) Prior Publication Data
US 2013/0337493 A1    Dec. 19, 2013

Related U.S. Application Data

(60) Provisional application No. 61/420,981, filed on Dec. 8, 2010, provisional application No. 61/375,340, filed on Aug. 20, 2010.

(51) Int. Cl.
*G01N 31/00* (2006.01)
*G01N 31/22* (2006.01)
*G01N 30/88* (2006.01)
*G01N 21/31* (2006.01)
*G01N 30/60* (2006.01)
*G01N 30/00* (2006.01)
*H01J 49/44* (2006.01)
*G01N 30/22* (2006.01)
*G01N 27/447* (2006.01)
*H01J 49/00* (2006.01)
*G01N 35/00* (2006.01)

(52) U.S. Cl.
CPC ............... *G01N 31/00* (2013.01); *G01N 21/31* (2013.01); *G01N 27/44717* (2013.01); *G01N 30/88* (2013.01); *G01N 31/22* (2013.01); *G01N 30/6091* (2013.01); *G01N 2030/77* (2013.01); *G01N 2035/00158* (2013.01); *H01J 49/00* (2013.01)

(58) Field of Classification Search
None
See application file for complete search history.

(56) References Cited

U.S. PATENT DOCUMENTS

| 7,586,102 | B2 * | 9/2009 | Mourtada et al. | ....... 250/432 PD |
|---|---|---|---|---|
| 2005/0061983 | A1 | 3/2005 | Stonger et al. | |
| 2005/0176012 | A1 | 8/2005 | Wozny et al. | |
| 2005/0271654 | A1 | 12/2005 | Rinderknecht et al. | |
| 2007/0154895 | A1 * | 7/2007 | Spaid et al. | ....... 435/6 |
| 2008/0035542 | A1 | 2/2008 | Mourtada et al. | |
| 2008/0140046 | A1 | 6/2008 | Buck et al. | |
| 2008/0149847 | A1 * | 6/2008 | Casale et al. | ....... 250/432 R |
| 2008/0218752 | A1 | 9/2008 | Hagler | |
| 2008/0224072 | A1 | 9/2008 | Sonnenhol et al. | |
| 2008/0226552 | A1 * | 9/2008 | Powell et al. | ....... 424/1.85 |
| 2009/0155167 | A1 | 6/2009 | Powell et al. | |
| 2009/0253587 | A1 | 10/2009 | Fernandez | |
| 2010/0145630 | A1 | 6/2010 | Ball et al. | |

FOREIGN PATENT DOCUMENTS

| WO | 2008083313 A1 | 7/2008 |
|---|---|---|
| WO | 2008083313 A2 | 7/2008 |
| WO | 2008110757 A1 | 9/2008 |
| WO | 2009100428 A1 | 8/2009 |
| WO | 2010065810 A1 | 6/2010 |
| WO | 2010065810 A2 | 6/2010 |
| WO | 2013012822 A1 | 1/2013 |

OTHER PUBLICATIONS

Muramatsu, Y. et al. 2004. Studies with natural and anthropogenic iodine isotopes: iodine distribution and cycling in the global environment. Journal of Environmental Radioactivity 74: 221-232. specif. p. 223.*

Elizarov, A.M. et al. Feb. 2010. Design and optimization of coin-shaped microreactor chips for PET radiopharmaceutical synthesis. Journal of Nuclear Medicine 51: 282-287. specif. pp. 282, 284.*

Abgrall, P. et al. 2007. Lab-on-a-chip technologies: making a microfluidic network and coupling it into a complete microsystem—a review. Journal of Micromechanics and microengineering 17: R15-R49. specif. pp. R15, R36, R37.*

Kapil, M. et al. 2013. A Review: Residual solvents and various effective gas chromatographic techniques in the analysis of residual solvent. International Journal of Pharma Research & Review. Oct. 2(10): 25-40. specif. p. 25.*

(Continued)

*Primary Examiner* — Renee Claytor
*Assistant Examiner* — Sharon M Papciak
(74) *Attorney, Agent, or Firm* — Lucas Divine; General Electric Company

(57) ABSTRACT

A quality control ("QC") system for PET or SPECT radiopharmaceuticals is disclosed that contains a disposable, no-leakage, self-contained QC cassette, which interfaces with the QC system. The QC system may include a shield that substantially surrounds the cassette such that the area and the cassette are both shielded. The QC cassette may contain shielding also. The QC cassette contains components for conducting one or more QC tests. These components include sensor and devices for performing various QC tests on radiopharmaceuticals. The QC system may contain a number of sub-systems and devices for supporting the QC tests. The QC system may produce a QC report containing the test results.

20 Claims, 14 Drawing Sheets

(56) References Cited

OTHER PUBLICATIONS

Heiden, et.al. Comparison of Dieffferent Approaches to Rapid Screening of Headspcase Samples: Pros and Con using MS-Based Electronic Noses verus Chromatography, Aug. 2002. retrieved on Dec. 30, 2011 from interent.

Taddeo, automated module for syntheses of therapeutic radiopharmaceuticals Jan. 2010, retrieved on Dec. 30, 2011 from internet.

PCT/2011/048564-ISRWO dated Jan. 25, 2012.

Partial EP Search Report from Corresponding PCT Application PCT/US2011/0458564; dated Apr. 22, 2015; 7 pages.

Altria et al., "A gamma-ray detector for capillary zone electrophoresis and its use in the analysis of some radiopharmaceuticals", Electrophoresis, vol. No. 11, Issue No. 9, pp. 732-734, Jan. 1, 1990.

Westerberg et al., "beta<+>—Selective radiodetector for capillary electrophoresis", Journal of Chromatography, vol. No. 645, Issue No. 2, pp. 319-325, Aug. 20, 1993.

Ding et al., "Separation of Nonionic Compounds by CE Using a Lauryl Poly(oxyethylene) Sulfate Additive", Analytical Chemistry, vol. No. 69, Issue No. 8, pp. 1593-1597, Apr. 15, 1997.

Klunder et al., "Analysis of Fission Products Using Capillary Electrophoresis With On-Line Radioactivity Detection", Analytical Chemistry, vol. No. 69, Issue No. 15, pp. 2988-2993, Aug. 1, 1997.

Jankowsky et al., "Determination of dissociation constants of 99m Technetium radiopharmaceuticals by capillary electrophoresis", Journal of Chromatography A, vol. No. 833, pp. 83-96, 1999.

Vogt et al., "Separation of metal ions by capillary electrophoresis—diversity, advantages, and drawbacks of detection methods", Fresenius J. Anal. Chem., vol. No. 370, pp. 316-331, Jun. 1, 2001.

Fritz, "The role of organic solvents in the separation of nonionic compounds by capillary electrophoresis", Electrophoresis, vol. No. 24, pp. 1530-1536, 2003.

Stachowiak et al., "Chip electrochromatography", Journal of Chromatography A, vol. No. 1044, pp. 97-111, 2004.

Zaggout et al., "Encapsulation of methyl orange pH-indicator into a sol-gel matrix", Materials Letters, vol. No. 59, pp. 2928-2931, 2005.

Wu et al., "Electrophoretic separations on microfluidic chips", Journal of Chromatography A, vol. No. 1184, pp. 542-559, 2008.

European Search Report and Written Opinion issued in connection with corresponding EP Application No. 11818882.0-1554 dated Aug. 20, 2015.

\* cited by examiner

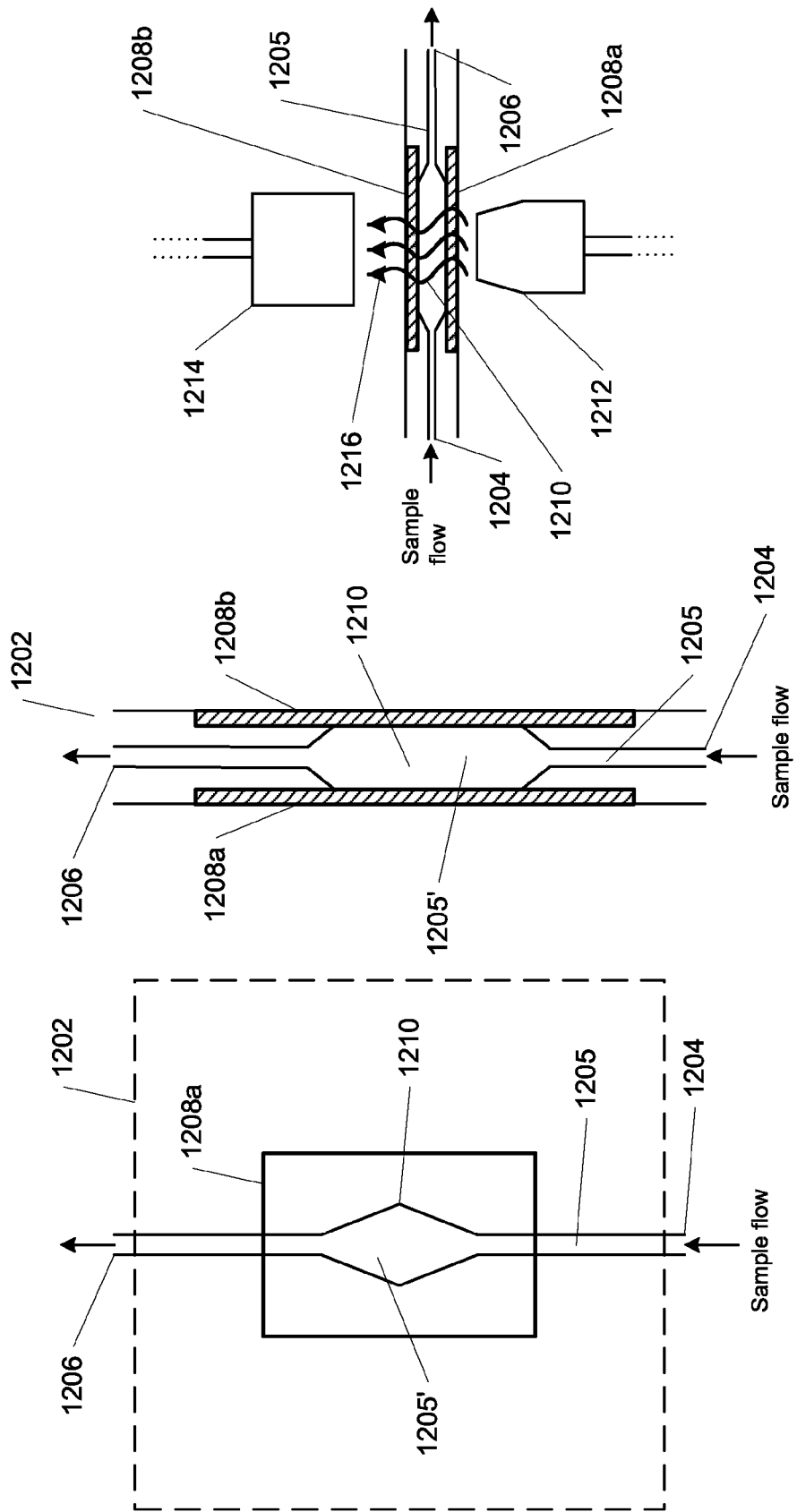

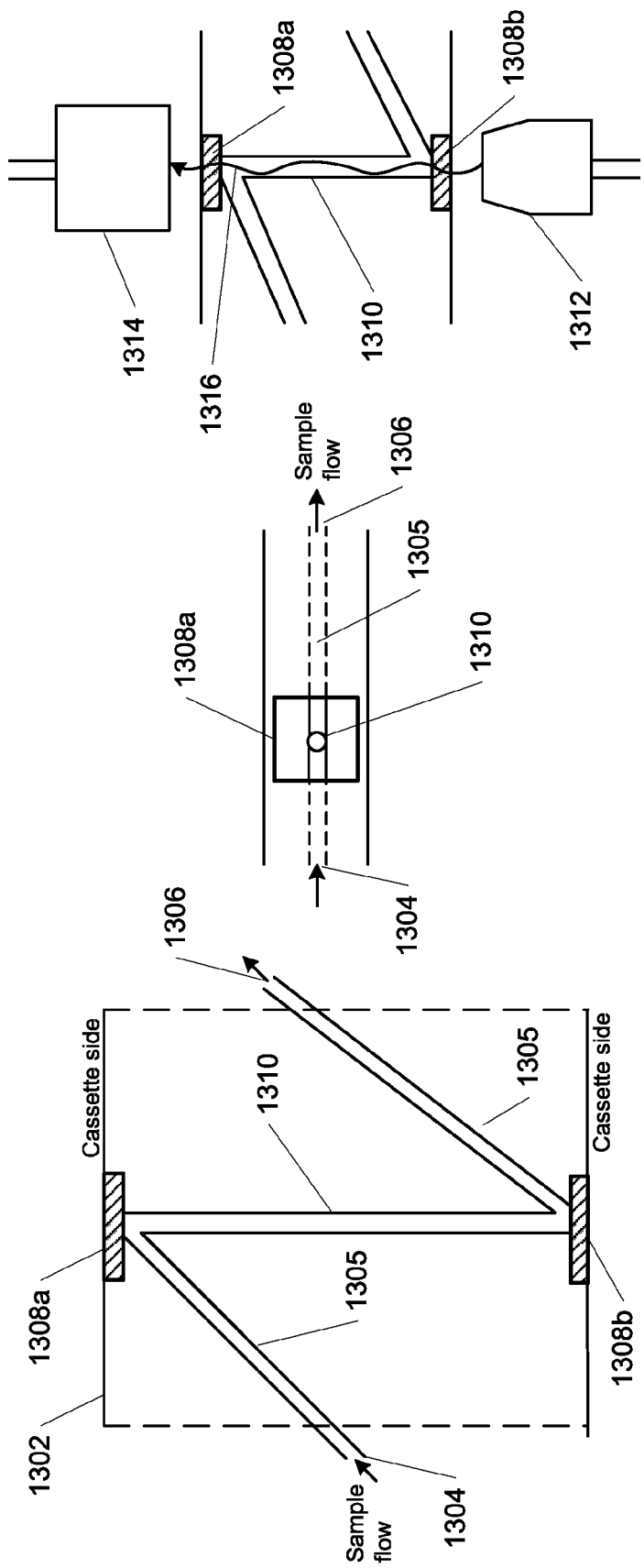

QUALITY CONTROL DEVICES AND METHODS FOR RADIOPHARMACEUTICALS

CROSS-REFERENCE TO RELATED APPLICATIONS

This application is a filing under 35 U.S.C. 371 of international application number PCT/US2011/048564, filed Aug. 22, 2011, which claims priority to U.S. application No. 61/375,340 filed Aug. 20, 2010 and to U.S. application No. 61/420,981 filed Dec. 8, 2010, the entire disclosure of which is hereby incorporated by reference.

FIELD OF THE INVENTION

The present invention relates to quality control systems and methods for their use in ensuring the quality of radiopharmaceuticals, such as radiopharmaceuticals used in Positron Emission Tomography (PET) and Single-Photon Emission Computed Tomography (SPECT).

BACKGROUND

PET and SPECT imaging systems are increasingly used for detection of diseases and are useful in providing early detection and a definite diagnosis for such diseases (e.g., disease states within oncology and neurology). For example, currently, a large percentage of PET and SPECT tests are related to cancer detection and early Alzheimer detection. These diseases require early diagnosis to allow a timely and effective treatment.

PET and SPECT imaging systems create images based on the distribution of positron-emitting isotopes and gamma emitting isotopes, respectively, in the tissue of a patient. The isotopes are typically administered to a patient by injection of radiopharmaceuticals including a probe molecule having a positron-emitting isotope, e.g., carbon-11, nitrogen-13, oxygen-15, or fluorine-18, or a gamma radiation emitting isotope, e.g. technetium-99. The radiopharmaceutical is readily metabolized, localized in the body or chemically binds to receptor sites within the body. Once the radiopharmaceutical localizes at the desired site (e.g., chemically binds to receptor sites), a PET or SPECT image is generated.

Examples of known radiopharmaceuticals include $^{18}$F-FLT ([$^{18}$F]fluorothymidine), $^{18}$F-FDDNP (2-(1-{6-[(2-[$^{18}$F]fluoroethyl)(methyl)amino]2-naphthyl}ethylidene)malonitrile), $^{18}$F-FHBG (9-[4-[$^{18}$F]fluoro-3-(hydroxymethyl)butyl]guanine or [$^{18}$F]-penciclovir), $^{18}$F-FESP ([$^{18}$F]-fluoroethylspiperone), $^{18}$F-p-MPPF (4-(2-methoxyphenyl)-1-[2-(N-2-pyridinyl)-p-[18p]fluorobenzamido]ethylpiperazine) and $^{18}$F-FDG ([$^{18}$F]-2-deoxy-2-fluoro-D-glucose).

Radioactive isotopes in radiopharmaceuticals are isotopes exhibiting radioactive decay, for example, emitting positrons. Such isotopes are typically referred to as radioisotopes or radionuclides. Exemplary radioisotopes include $^{18}$F, $^{124}$I, $^{11}$C, $^{13}$N and $^{15}$O, which have half-lives of 110 minutes, 4.2 days, 20 minutes, 10 minutes, and 2 minutes, respectively.

Because radioisotopes have such short half-lives, the synthesis and purification of the corresponding radiopharmaceutical must be rapid. Quality control (QC) assessments on the radiopharmaceutical must also take place in a short period of time. Preferably, these processes (i.e., synthesis, purification, and QC assessment) should be completed in a time well under the half-life of the radioisotope in the radiopharmaceutical. Presently, QC assessments may be relatively slow mainly due to the fact that they are conducted manually. Accordingly, the time involved in QC assessments can be a bottleneck that hampers the growth of this important area of medicine. These assessments may include pH measurement; visual inspection (e.g., for color and the presence of solids); radiochemical purity; radiochemical identity; radionuclide purity test; chemical purity test; specific activity test; test of the integrity of the sterile filter membrane; sterility test (typically completed after release); and bacterial endotoxin test (e.g., limulus amebocyte lysate test or LAL for short).

Because radionuclides have such short half-lives and the QC assessments are potentially numerous, there is a need for systems, components, and methods for reducing running time for the QC assessments. The embodiments of the present invention provide such systems, components, and methods.

SUMMARY

An exemplary embodiment is a quality control system with a port configured to operatively receive and engage a cassette configured with one or more analysis components, and one or more sub-systems, that have one or more computer processors configured to interface with the one or more analysis components causing the one or more analysis components to conduct analysis of a sample of a radiopharmaceutical contained in the cassette, collect data from the analysis components, and provide an output of one or more results based upon the data.

Another exemplary embodiment is a cassette having an intake reservoir for input of a fluid sample of a radiopharmaceutical, one or more analysis components, and a radioactive fluid waste reservoir.

Another exemplary embodiment is a method for quality control analysis of a PET tracer or radiopharmaceutical. The method includes injecting a sample comprising a radiopharmaceutical into a quality control system. The quality control system includes: a cassette comprising one or more analysis components and at least one radioactive waste reservoir, and a shield, substantially surrounding the cassette, that substantially reduces the escape of radiation from the system. The method further includes activating, by at least one computer processor, the one or more analysis components to conduct a quantitative analysis of the sample, obtaining, by the at least one computer processor, a measurement value from each of the one or more analysis components, comparing, by the at least one computer processor, each measurement value to a predetermined corresponding criterion value, generating an individual quality rating for each measurement value from each analysis component or a cumulative quality rating for the sample from each measurement value, and evaluating said individual quality rating or cumulative quality rating for the sample. Upon the individual quality rating or cumulative quality rating falling above or below a predetermined individual or cumulative quality rating value or falling outside of an established range, the sample fails the quality control analysis.

Another exemplary embodiment is a method for determining the location and/or concentration of one or more radioactive compounds in a capillary electrophoresis column comprising. The method includes conducting capillary electrophoresis with a sample comprising one or more radioactive compounds; electronically monitoring the progress of the electrophoresis with a two-dimensional gamma detector; stopping the electrophoresis when a first radioactive compound reaches a critical point; collecting gamma detector data by at least one computer processor; and automatically correlating said gamma detector data to the location and/or concentration of the one or more radioactive compounds.

Another exemplary embodiment is a quality control system including an enclosed, disposable fluid path and one or more sub-systems comprising one or more computer processors configured to interface with one or more analysis components that interact with the disposable fluid path causing the one or more analysis components to conduct analysis of a sample, contained entirely with the fluid path, collect data from the analysis components, and provide an output of one or more results based upon the data Another exemplary embodiment is a radiopharmaceutical dispensing system including a fluid flow path comprising one or more valves for fluidly routing a fluid. The dispensing system further includes a motive device fluidly coupled to the fluid path to apply a motive force to the fluid in the fluid flow path, and a cassette fluidly coupled to the fluid flow path including one or more analysis components for conducting an analysis of a sample that is a predetermined volume of the fluid.

Another exemplary embodiment is a cassette having an intake reservoir for receiving a volume of a sample of a radiopharmaceutical. The cassette includes analysis components for conducting a pH test, a limulus amebocyte lysate test, a radiochemical purity analysis test, a K222 test, and a visual appearance test. The cassette has one or more fluidic flow paths fluidically coupling the intake reservoir and each of the analysis components. The cassette is disposable and is configured to operatively interface with an external system having an interrogator to enable conduct of at least the radiochemical purity test.

Another exemplary embodiment is a method for accepting an input of a sample of a radiopharmaceutical through an intake reservoir of a disposable cassette. The sample is caused to be fluidically distributed along one or more fluidic pathways to a sample input location located at each of a plurality of analysis components located on the disposable cassette. The analysis components include: a pH test, a limulus amebocyte lysate test, a radiochemical purity analysis test, a K222 test, and a visual appearance test, wherein further the fluid distribution initiates the performance of the tests. The sample is impinged upon by signals from signal sources. The results of tests on the disposable cassette are observed. The results of the pH test, the limulus amebocyte lysate test, the radiochemical purity analysis test, and the K222 test are determined through comparison to one or more reference samples.

BRIEF DESCRIPTION OF THE DRAWINGS

FIGS. 12A, 12B, and 12C depict a pH measurement cell according to an exemplary embodiment.

FIGS. 13A, 13B, and 13C depict an alternative pH measurement cell according to an exemplary embodiment.

Figure 1:
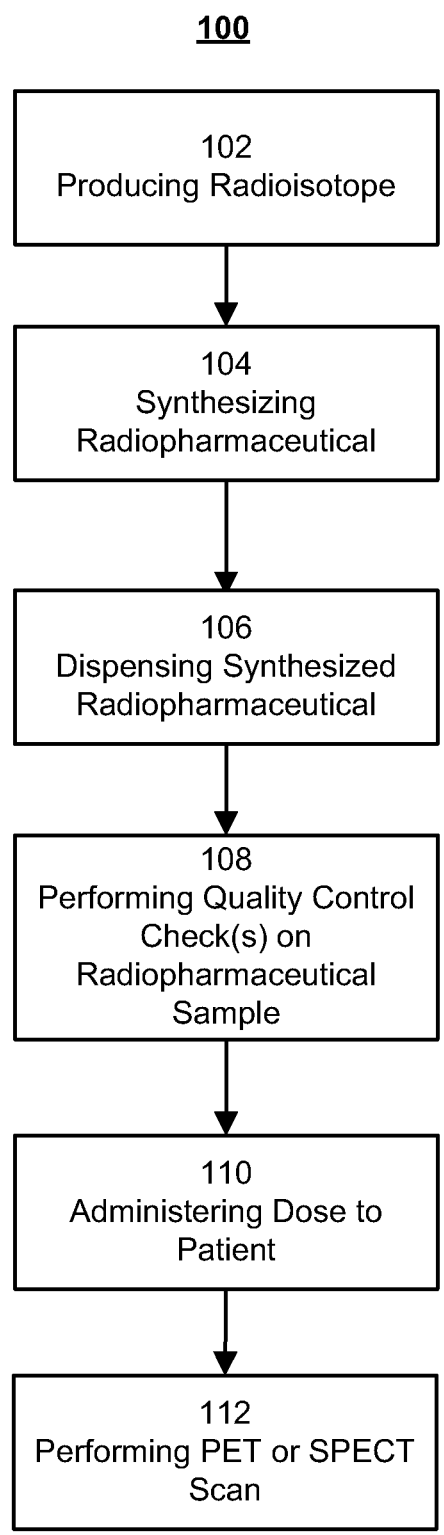
FIG. 1 depicts a method for producing and using a PET or SPECT imaging agent according to an exemplary embodiment of the invention.

These and other embodiments and advantages of the invention will become apparent from the following detailed description, taken in conjunction with the accompanying drawings, illustrating by way of example the principles of the various exemplary embodiments of the invention.

DETAILED DESCRIPTION OF THE PREFERRED EMBODIMENTS

It will be readily understood by those persons skilled in the art that the embodiments of the inventions described herein are capable of broad utility and application. Accordingly, while the invention is described herein in detail in relation to the exemplary embodiments, it is to be understood that this disclosure is illustrative and exemplary of embodiments and is made to provide an enabling disclosure of the exemplary embodiments. The disclosure is not intended to be construed to limit the embodiments of the invention or otherwise to exclude any other such embodiments, adaptations, variations, modifications and equivalent arrangements.

The following descriptions are provided of different configurations and features according to exemplary embodiments of the invention. These configurations and features may relate to providing systems and methods for quality control of radiopharmaceuticals and other compounds or formulations containing radioisotopes. While certain nomenclature and types of applications or hardware are described, other names and application or hardware usage is possible and the nomenclature provided is done so by way of non-limiting examples only. Further, while particular embodiments are described, these particular embodiments are meant to be exemplary and non-limiting and it further should be appreciated that the features and functions of each embodiment may be combined in any combination as is within the capability of one of ordinary skill in the art.

The figures depict various functionality and features associated with exemplary embodiments. While a single illustrative block, sub-system, device, or component is shown, these illustrative blocks, sub-systems, devices, or components may be multiplied for various applications or different application environments. In addition, the blocks, sub-systems, devices, or components may be further combined into a consolidated unit. Further, while a particular structure or type of block, sub-system, device, or component is shown, this structure is meant to be exemplary and non-limiting, as other structure may be able to be substituted to perform the functions described.

Exemplary embodiments of the invention relate to a quality control ("QC") system that contains a disposable, "no-leakage" or leak-tight, self-contained cassette, which sits in an area within or is communicatively attached to the QC system. The cassette may contain shielding to prevent or minimize radiation exposure from the contents of cassette, such as a radiopharmaceutical. The QC system may itself include a shield that substantially surrounds the cassette. The cassette, in turn, contains one or more components for conducting various quality control tests. For example, there may be a component for determining pH, a component for determining chemical purity, a component for determining radiochemical purity/radionuclidic purity, a component for determination of appearance (e.g., color, clarity/opacity, and the presences of particles), a component for determination of the presence of Kryptofix ("K222") by colorimetry, and a reservoir or other container for collection of waste. The waste reservoir may be contained on the cassette or it may be external to the cassette, such as part of the QC system. Additionally, separate from the cassette, the QC system may contain sub-systems or device, such as a head-space mass spectrometer ("HS-MS or a gas-chromatography ("GC") for determination of the presence of residual solvents. The HS-MS and the GC, when present, may each include their own or common sampling and waste handling sub-systems.

According to exemplary embodiments, the cassette may contain a number of components, with the ability to miniaturize the components to fit onto the cassette being an important factor. According to some embodiments, one or more of the components, such as the pH, appearance and purity components, may be provided as part of a "lab on a chip" ("LOC") variant, in which a planar body includes fluidpaths and reservoirs where different properties may be measured. However, these components need not all be on the same LOC or even in an LOC format.

The QC system may either be separate from a synthesis system or may be an integral part of the synthesis system for a radiopharmaceutical. For example, the QC system may be coupled to a synthesis system such as the FASTlab system from GE Healthcare. The synthesis system may produce radiopharmaceuticals for use with either PET or SPECT scanners. The QC system may be coupled to a drug dispensing system for the synthesized compounds. Alternatively, the QC system may be a stand-alone system capable of performing QC analysis for any synthesis or dispensing system manufactured by companies other than GE Healthcare. It should be appreciated that the use of the term "radiopharmaceutical", "radiotracer", "PET tracer", or "SPECT tracer" herein is meant to be exemplary and non-limiting and the mention of one term does not exclude substitution of the other terms in the described embodiment.

The cassette includes hardware for separating a sample of fluid from a bulk supply and channeling it into or among one or more components for testing. Each component may contain appropriate devices for observing, testing, and analyzing the sample that is inside the cassette. In some embodiments, such devices may be a part of the QC system, external to the cassette.

The QC system may include computer hardware and software for data logging of all sensors, determination of all measured parameters, reporting the results based upon required parameters as determined by applicable regulations, such as determining if the sample is within regulatory compliance; performing automatic control of the results against current drug product specifications, for example checking that results fall within predetermined acceptance ranges; and reporting the results. For example, results may be reported as "Pass" or "Fail." Alternatively, the results may be reported as a total numeric score, which, if it falls under or over a certain value, can be considered as a "failing" score indicating that the sample may not be usable for administration to a patient. Further, the QC system and cassette may include sufficient hardware and software to allow all components and sub-systems to be calibrated, controlled and validated.

Additionally, the QC system and each component may contain and/or interface with a waste reservoir or sub-system for safe handling of all radioactive fluid wastes, such as after a particular QC test has been performed. These radioactive wastes may include waste coming from the cassette and/or a manifold and/or from the HS-MS or GC component and/or any other testing devices, components, or sub-systems. The cassette itself may be considered a waste reservoir or receptacle since it may be disposable.

The QC system may have different configurations. In exemplary embodiments, the QC system may be a miniaturized, bench-top-size or smaller system. The QC system may be a stand-alone system. The sample may be obtained from the output of a synthesizer as described herein. The sample may be manually or automatically input into the QC system. For example, a syringe may be used to extract a sample amount from a bulk supply and then input the sample into the QC system. Such input may occur through an intake or injection reservoir or container. For example, a dose vial of the radiopharmaceutical may be tapped directly by the QC system to extract the desired sample. A syringe pump or other extraction device may be used. Alternatively, the QC system may be integrated with or fluidly coupled to a radiopharmaceutical synthesizer system. The fluid coupling may be through a manifold or another type of tubing connection. In this embodiment, a sample of the synthesized radiopharmaceutical may be output directly from the synthesizer directly into the QC system. In an integrated embodiment, the QC system may be a part of the synthesizer. The sample may be obtained directly from the synthesizer's output of the radiopharmaceutical.

According to exemplary embodiments, the present invention may incorporate one or more of the following features: a single "no leakage" LOC cassette or chip (e.g., manufactured on a silicon wafer, on a glass plate or on a suitable card made from a polymer, such as a single co-polymer, or a conventional microchip which defines an elongate flow path between two planar and transparent substrates) that can support quantification of up to eight QC parameters, in some embodiments, while ensuring that no radioactive fluid waste leaves the cassette. In addition, such a QC system may also include a hardware unit to operate sensors to quantify the QC parameters, log the data, and give the operator the signal to proceed. Further, such a QC system would not have to be placed in a hot cell, as the cassette and/or the QC system could itself contain an integrated shield. Finally, the QC system could also include an HS-MS sub-system and/or a GC sub-system in a single, fully automated hardware unit.

FIG. 1 depicts a flow chart of a method of synthesizing and using a PET or SPECT imaging agent and using a QC system according to an exemplary embodiment of the invention. The method 100 as shown in FIG. 1, may be executed or otherwise performed by one or a combination of various systems, components, and sub-systems, including a computer implemented system. Each block shown in FIG. 1 represents one or more processes, methods, and/or subroutines carried out in the exemplary method 100.

At block 102, a radioisotope is produced. The radioisotope (e.g., $^{18}F$ or $^{11}C$) is typically produced using a cyclotron (e.g., GE PETtrace 700 cyclotron) for PET radioisotopes or using a generator for SPECT radioisotopes (e.g., to produce the $^{99}$Tc). The cyclotron or generator may be located at a manufacturing site or it may be located in proximity to the scanner. Locating the cyclotron or generator on-site with the PET or SPECT scanner minimizes transportation time for the radioisotope. It should be appreciated that while "PET" and "SPECT" are referred to herein such examples are exemplary and the mention of one does not preclude application to the other.

At block 104, a radiopharmaceutical is synthesized using the radioisotope. A synthesizer is used to combine the radioisotope with a radioligand. The result is a radiopharmaceutical. The synthesizer may be manually operated, semi-automated in operation, or fully automated. For example, the GE Healthcare Fastlab system is a fully automated synthesizer. The synthesizer is generally operated in a "hot cell" to shield the operator from the radioactivity of the radioisotope.

At block 106, the synthesized radiopharmaceutical is dispensed. The doses of the radiopharmaceutical are dispensed into collecting vials for patient administration and for QC. As described above, a sample of the bulk synthesized radiopharmaceutical may be dispensed directly into a QC system and/or cassette for QC testing as described herein.

At block 108, quality control checks on a radiopharmaceutical sample are performed. There may be one or more QC checks performed. According to exemplary embodiments of the invention, these checks may be automated. A QC system of the present invention may be used. The QC system may include a cassette having a plurality of components for performing the tests. The QC system may be a stand-alone system or it may be integrated with the synthesizer described above. Radiopharmaceutical doses are dispensed from the synthesizer. Sample(s) from one or more dispensed vials may be selected for QC checks. These samples may be input to the QC system. Alternatively, the QC system may be connected or coupled to the synthesizer such that an appropriate sample may be directly output from the synthesizer to the QC system. In some embodiments, the sample for QC checks may be input into or onto the cassette. The cassette may then be manually or automatically input to the QC system.

At block 110, a dose from the same production batch as the sample on which the QC tests were conducted is administered to a patient.

At block 112, a PET or SPECT scan is performed on the patient who received the dose.

Figure 2:
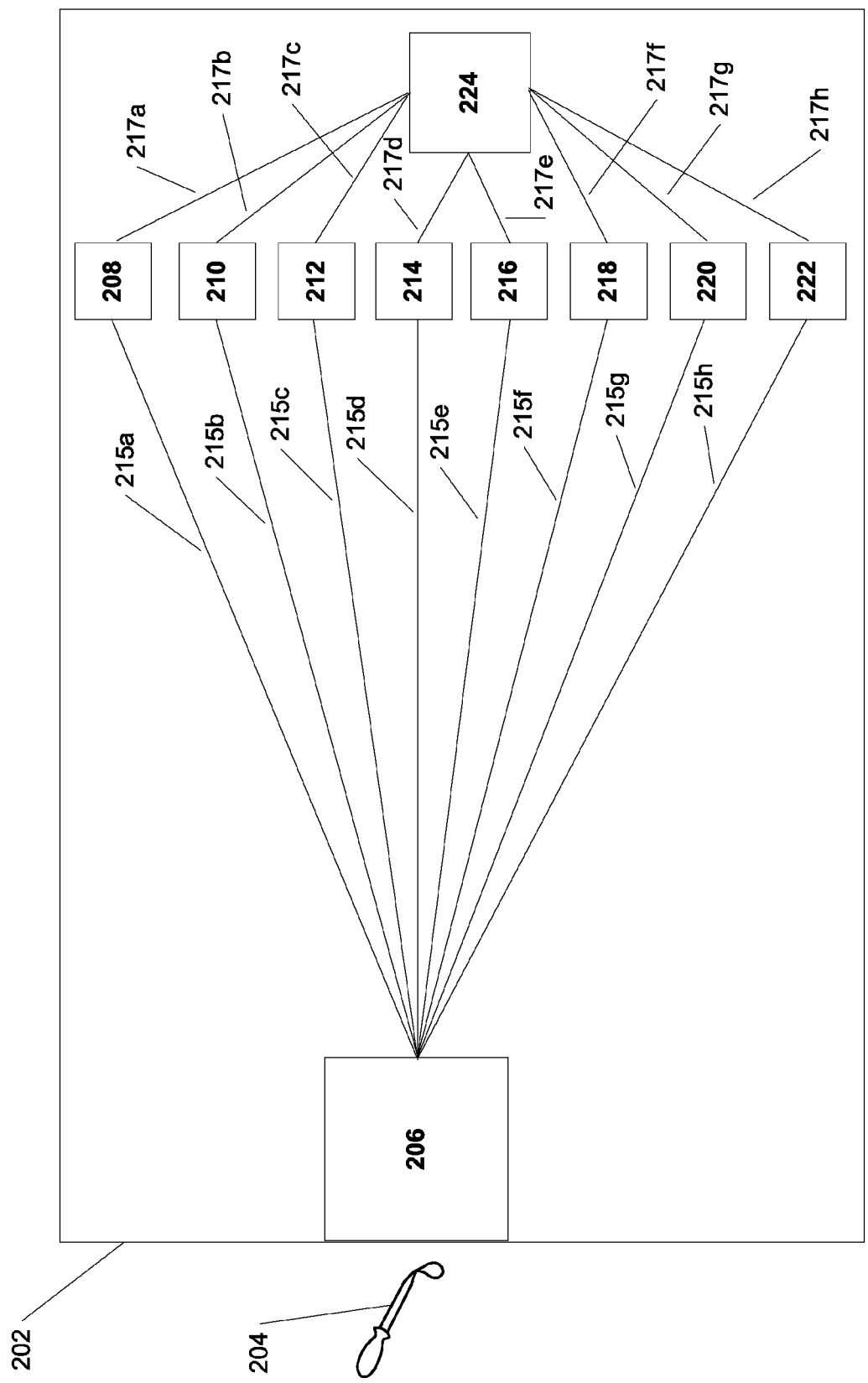
FIG. 2 depicts a cassette with components for quality control testing according to an exemplary embodiment of the invention.

FIG. 2 depicts a cassette with quality control components according to an exemplary embodiment of the invention. The cassette is preferably disposable thus allowing a new cassette to be provided for subsequent QC testing of samples and, according to exemplary embodiments, contains a plurality of QC testing components, such as components 208, 210, 212, 214, 216, 218, 220, and 222. The cassette 202 contains an intake reservoir or well 206 in fluid communication with a waste reservoir or well 224 individually across each of components 208, 210, 212, 214, 216, 218, 220, and 222 via fluid paths 215a-h and 217a-h. Cassette 202 is also contemplated to be formed using overlying planar substrates which define fluid paths 215a-h, 217a-h with components 208, 210, 212, 214, 216, 218, 220, and 222 therebetween. For example, a channel or groove may be cut or etched into an upper and a lower substrate which forms an enclosed fluid path when the substrates are mated. Reservoirs 206 and 224 are desirably open through the upper substrate, thus allowing provision of a fluid sample into reservoir 206. These reservoirs are "open" to the extent required to receive or exhaust a fluid into or out of the cassette. Seals and/or valves may be used to open and close these reservoirs to preserve the leak tight environment of the cassette 202. Likewise, the cassette 202 may have other seals and/or valves capable of being opened to access the contents of the cassette 202, such as reagents and solvents contained in the components described herein. The fluid paths allow for the fluid be motively directed into components 208, 210, 212, 214, 216, 218, 220, and 222, and to be then directed through fluid paths 217a-h into the waste reservoir 224. It should be appreciated that the cassette 202 may contain more or less components than shown. The components shown are exemplary and meant to be non-limiting. In some embodiments, the cassette 202 may be modular and the components therein may be modules that may be removed such that the cassette's configuration may be altered. The cassette 202 is desirably made from a material that is capable of withstanding prolonged exposure to any of the various chemicals issuing from the synthesizer and used for the various QC tests supported by the components. For example, the cassette 202 may be manufactured using a silicon wafer, a glass plate, or a suitable card made from a polymer, such as a single co-polymer. The cassette 202 is preferably a "no-leakage" structure such that the various components contained on the cassette (e.g., the chemicals necessary for the determination of pH on the cassette, such as pH indicators) and the sample applied to the cassette 202 do not leak outside of the cassette and, according to exemplary embodiments, do not travel outside of the cassette once placed into the cassette 202.

Figure 3:
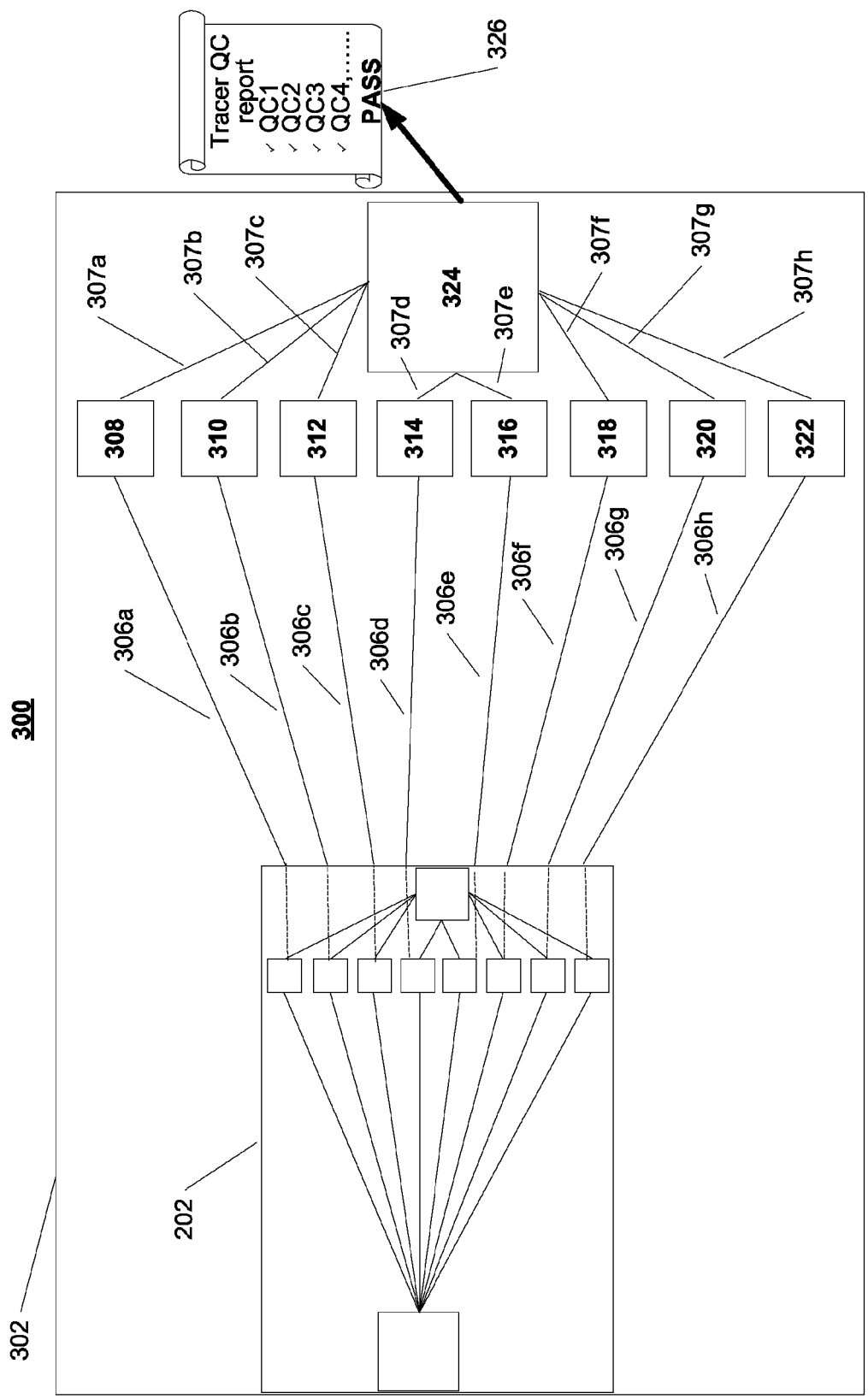
FIG. 3 depicts a system for performing quality control testing using the cassette according to an exemplary embodiment of the invention.

The cassette 202 is preferably designed to be input into or incorporated into a system for quality control, such as the QC system shown in FIG. 3. Insertion into the QC system may be required to activate the cassette to enable the performance of the QC tests supported by the cassette 202. In this regard, the cassette 202 may be designed to interface with a QC system. For example, the cassette 202 may have various contacts and connections supporting such an interface. These contacts enable activation of the cassette, performance of the QC tests, and collection of data therefrom. The contacts may be electrical or electronic. It should be appreciated that the cassette 202 may interface with the QC system in other manners. For example, the cassette 202 may interface visually with the QC system enabling visual observation of various QC tests by sensors in the QC system. The cassette 202 may engage with or be coupled to the QC system in a manner such that the cassette 202 is not required to be inserted into the QC system that is, the interface may be external to the QC system. For example, a cable may be attached to the cassette 202 to engage or communicatively couple with the QC system.

Furthermore, the cassette 202 is desirably disposable such that it provides a single use fluid path for QC testing of a sample. For example, following use of the cassette 202, it may be appropriately disposed of. The cassette 202 may contain sufficient shielding to prevent or minimize radiation exposure. Additionally, each cassette 202 may be configured for use with a particular radiopharmaceutical or for the performance of only certain QC assessments (e.g., only pH; radiochemical purity; radiochemical identity, and chemical purity test and not radionuclide purity test or sterility test). It should be further appreciated that the QC system may contain sensors and other devices required to conduct a particular QC test. For example, the QC system may have a UV-Vis light source and detector. The cassette 202 may be operably positioned in the QC system to allow the light source to radiate the fluid and the detector to detect the transmitted or emitted radiation.

A sample 204 of a radiopharmaceutical is provided to the cassette 202. The sample 204 is preferably a fluid. The sample may be a radiotracer or radiopharmaceutical. The sample may be applied to the cassette 202 using a number of methods. For example, the sample 204 may be applied via injection using a syringe, such as a microliter ("µl") syringe, through a dropper, or through a manifold connected to a dispensing system. Other inputs may be used to apply the sample 204. The sample input may be automatically or manually performed. A specific quantity of the sample 204 may be applied to the cassette 202. The quantity applied is desirably a sufficient amount to support performance of each of the QC tests supported by components of the cassette 202. It should be appreciated that the quantity required for QC testing is typically a small or minor volume of the overall batch or dose. In that case of a sample being used from a dose, the dose may still contain sufficient volume to administer to a patient. The sample 204 may be applied to or input to the cassette 202 at an intake reservoir 206. The intake reservoir 206 may be a container for the fluid volume of the sample 204. The intake reservoir 206 may be the starting point for distribution and routing of the fluid volume of the sample 204 to the various testing components of the cassette 202 via, e.g., tubing or microfluidic flow paths. These flow paths are preferably constructed of transparent material to permit observation of the sample and allow pass through of light sources used in performing certain QC tests. It should be appreciated that the entirely of the flow path is not required to be transparent and particular portions may be non-transparent or opaque. The intake reservoir 206 may have one or more valves and/or pumps to support distribution of the sample 204. The intake reservoir 206 may perform automatic distribution of the sample 204. The intake reservoir 206 may be configurable to support distribution of the sample 204 to all of the available QC testing components or to only a sub-set of the available QC testing components on the cassette 202. Alternatively still, the present invention contemplates that each of components 208, 210, 212, 214, 216, 218, 220, and 222 may have its own intake reservoir 206 and optionally even its own waste reservoir 224.

The cassette 202 desirably contains one or more components for performing QC tests. For example the cassette 202 contains components 208, 210, 212, 214, 216, 218, 220, and 222. Each component performs one or more QC tests. By way of non-limiting example, the component 208 may test pH; the component 210 may test radionuclidic purity ("RNP"); the component 212 may test radiochemical purity ("RCP"); the component 214 may test for the presence/absence or concentration of K222; the component 216 may test chemical purity; the component 218 may perform a test for the presence of bacteria, such as a limulus amebocyte lysate ("LAL") test; the component 220 may perform visual testing; and the component 222 may be a spare component or may perform other tests (e.g., dissolved and gaseous $O_2$ levels; dissolved and gaseous $CO_2$ levels; combined $O_2$/pH using, e.g., a SensorDish Reader, or contain a miniaturized HPLC as described in FIG. 14). As should be appreciated, other combinations of components are possible for conducting tests. It should be further appreciated that while an individual connection is shown between the intake reservoir 206 and each component in on the cassette 202 and the individual components are not shown as interconnected, certain components may be structured in series such that a sample volume is tested sequentially by two or more components. For example, the RNP and RCP components may be in line and located before the component for testing chemical purity. In such an embodiment, the intake reservoir 206 may be connected to the first testing reservoir. In addition, a single component may be used to perform two or more QC tests. For example, the RNP and RCP may be determined by the same component.

In some embodiments, the pH component, when present, includes an indicator (e.g., bromthymol blue) that changes color when the sample arrives at the pH testing component. The change in color may be detected visually or, in a preferred embodiment, spectrophotometrically using a micro UV-Vis spectrophotometer (UV-Vis light source and detector) adapted to sit in the cassette 202. In other embodiments, the pH component includes a sensor spot or a needle-type microsensor (PreSens GmbH, Regenrsburg, Germany).

In some embodiments, the RNP and RCP components, when present, include not only a chromatography unit (e.g., a miniaturized capillary electrophoresis (CE) unit, such as those described in Wu, et al., *J. Chromatogr. A* 1184: 542-559 (2008) or a miniaturized capillary electrochromatography (CEC) unit, such as those described in Stachowiak, et al., *J. Chromatogr. A* 1044: 97-111 (2004)) to separate the desired radiopharmaceutical from contaminants that may be present in the sample obtained from the synthesizer (e.g., starting materials), but also a detection unit (e.g., a radiochemical detector, such as those described in Jankowsky, et al., *J. Chromatogr. A* 833: 83-96 (1999)).

In some embodiments, the K222 component, when present, includes an iodoplatinate reagent that indicates the presence of as low as 2 µg/mL K222. K222, when present, causes the iodoplatinate reagent to change color from colorless/pink to blue-black. The change in color may be detected visually or, in a preferred embodiment, spectrophotometrically using a micro UV-Vis spectrophotometer (UV-Vis light source and detector) adapted to sit in or near the cassette 202.

In some embodiments, the chemical purity component includes a chromatography unit, such as the ones described above, or a high pressure/performance liquid chromatograph (HPLC), such as a miniaturized HPLC as described in FIG. 14. Regardless of the nature of the chromatography unit (i.e., CE, CEC or HPLC), the component also includes a detection unit, which is preferably a UV-Vis detector, adapted to sit in or near the cassette 202.

In some embodiments, the component that tests for the presence of bacteria, when present, includes a LAL test, preferably a turbidimetric or a chromogenic LAL test. For example, the turbidity may be measured using optical density over time for detection of coagulation of the reaction. The chromogenic test may be measured in the same manner as for UV-Vis type testing; that is, colorimetrically by a spectrophotometer.

In some embodiments, the testing component, when present, includes a charge-coupled device (CCD) sensor or a CCD micro camera (Medigus Ltd., Omer, Israel) capable of measuring the color and/or opacity of the sample.

According to exemplary embodiments, the cassette 202 has a waste reservoir 224 or be connected to a waste receptacle. The fluid waste may be collected internally as shown by the waste reservoir 224 or may be externally collected for disposal. The waste reservoir 224 may be configured to be emptied into an external waste receptacle. The waste reservoir 224 may be used to collect sample fluid following the various QC tests performed in the components as described above. The waste reservoir 224 may be a container of sufficient volume to contain the fluid volume of the sample. The waste reservoir 224 may be the same size container as the intake reservoir 206. In some embodiments, the waste reservoir 224 may be smaller since the fluid volume of the sample 204 may decrease as a result of the various QC tests. Certain QC tests performed may be destructive in nature such that a portion of the fluid volume of the sample 204 is destroyed in performing the testing. It should be appreciated that while an individual connection is shown between each QC testing component in the system 200 and the waste reservoir 224, certain QC testing components may be structured in series such that a sample volume is tested sequentially by two or more QC testing components. In such an embodiment, the waste reservoir 224 may be connected to the second or last testing component to receive the test volume.

FIG. 3 is a system for quality control using the cassette according to an exemplary embodiment of the invention. The system 300 consists of a QC system 302 and the cassette 202 (described above with regards to FIG. 2). The QC system 302 is a computer based system incorporating one or more computer processors, computer memory, computer storage, and software. The cassette 202 is desirably inserted into or otherwise communicatively coupled with the QC system 302. The cassette 202 is desirably configured as shown in FIG. 2, but could be configured in other ways according to various embodiments of the invention. The QC system 302 may be a stand-alone system or it may be integrated with other systems, such as a manifold system for dispensing radiopharmaceuticals as described herein. The QC system 302 performs QC testing through use of the cassette 202. That is, the QC system 302 causes the cassette 202 to perform the QC tests and record the results. The QC system 302 has equipment or structures for receiving, analyzing, and outputting data and results associated with the QC tests. The QC system 302 may have, or be associated with, one or more computer processors or processing machines, computer memory, input devices, output devices, and power supplies. These one or more computer processors may contain modules or executable software which enable the performance of the QC tests and analysis of the results from the components of the cassette 202. For example, the QC system 302 has sub-systems or devices 308, 310, 312, 314, 316, 318, 320, and 322. These sub-systems may represent interfaces with the components on the cassette 202. The sub-systems may be part of a single computer system and may commonly share one or more computer processors and/or computer memory. The sub-systems may be in electronic or electrical communication with one another. Alternatively, the QC system 302 may be communicatively coupled to one or more external computer systems through a wired connection and/or a wireless connection. The communicative coupling may be through a direct connection or over a computer based network.

The QC system 302 interfaces with the cassette 202 through one or more contact points 306a-h. For example, electrical or electronic contacts may be used. Visual contact may also be used. For example, certain tests are based upon visual observation of the sample or a reaction of the sample. Through such interfaces, the QC system 302 causes the cassette 202 to automatically perform its supported QC tests or observe the results of a QC test on the cassette 202. QC system 302 may further provide the means for providing motive input to the fluid of the cassette 202 so as to direct a sample fluid to one or more QC testing components thereon. This motive means may be in the form of power or other external influence to cause the fluid to be directed through the fluid paths on the cassette 202 as described above. As described above, the fluid, which may include a radiopharmaceutical, is desirably entirely contained within the cassette 202. The fluid is first transferred to or input into the cassette 202. Once there, the fluid is within the cassette 202. The cassette may be disposable to eliminate any cleaning or purging requirements for the QC system 302. Stated differently, the fluid may be confined to the cassette 202 during performance of the QC tests. The QC system 302 may have appropriate shielding to prevent or minimize radiation exposure.

Once the QC tests have been performed in the cassette 202, data is obtained from each cassette component by the sub-systems 308, 310, 312, 314, 316, 318, 320, and 322. Each of these sub-systems, as shown, is connected to or communicatively coupled through the interface to a respective component on the cassette 202. For example, the sub-system 308 is communicatively coupled to the component 208 through 306a, and so forth as depicted in FIG. 3. It should be appreciated that while individual connections are shown, a common connection or bus may be used for routing of data. The respective sub-systems may analyze the data from the test and evaluate the result.

Thus, for example, the cassette 202, as shown in FIG. 2, contains one or more components 208, 210, 212, 214, 216, 218, 220, and 222, where each component performs one or more QC tests. By way of non-limiting example, the component 208 may test pH and would be connected to or communicatively coupled through an interface to sub-system 308. Then, the component 210 may test radionuclidic purity ("RNP") and would be connected to or communicatively coupled through an interface to sub-system 310, and so on and so forth. These sub-systems and devices may represent hardware, software, or a combination thereof that interfaces with the components on the cassette. These sub-systems and devices may represent parts of a computer or similar processing machine. In some embodiments, each sub-system may have a computer processor The testing results are collected by a main sub-system 324 from each of the other sub-systems using connections 307a-h. The main sub-system 324 desirably consolidates the results and produces a QC report 326. The QC report 326 may provide an overall QC result such as "PASS" or "FAIL." The QC report 326 may provide details of the individual QC tests conducted in addition to the overall result.

The QC report 326 may be output as a hard copy report. For example, the QC report 326 may be printed out by an output device communicatively coupled to the QC system 302, such as a printer. Alternatively, the QC report 326 may be output in an electronic format. For example, the QC system 302 may have an electronic display for displaying the QC report 326 in an electronic format. The QC report 326 may be electronically saved. The main sub-system 324 may have electronic storage. For example, the main sub-system 324 may have solid state storage, both temporary, such as random access memory and permanent such as flash memory or hard disk type storage. It should also be appreciated that the QC system 302 may have input devices to allow for user interaction with the system 300. These input devices may be communicatively coupled to the main sub-system 324. For example, the QC system may have a QWERTY type keyboard, an alpha-numeric pad, and/or a pointing input device. Combinations of input devices are possible. The QC system 302 may be communicatively coupled to a computer network. For example, the QC system 302 may be communicatively coupled to a local area network or similar network. In some embodiments, the QC system may be communicatively coupled to the Internet. The QC system 302 may be wirelessly connected to the computer network or may be connected by a wired interface. The QC system 302 may transmit and receive data over the computer network.

It should be appreciated that while certain sub-systems, devices, and connections have been described, these sub-systems and devices may be combined into a single sub-system or device or structured into less or more sub-system than described. Routing of the data is shown in one particular configuration, however this routing is exemplary only.

Following completion of the QC testing, the cassette 202 is removed from the QC system 302. For example, the cassette 202 may be ejected from the QC system 302. The cassette 202 may be disposed of following use in accordance with handling procedures for the residual radiopharmaceutical contained therein.

Figure 4:
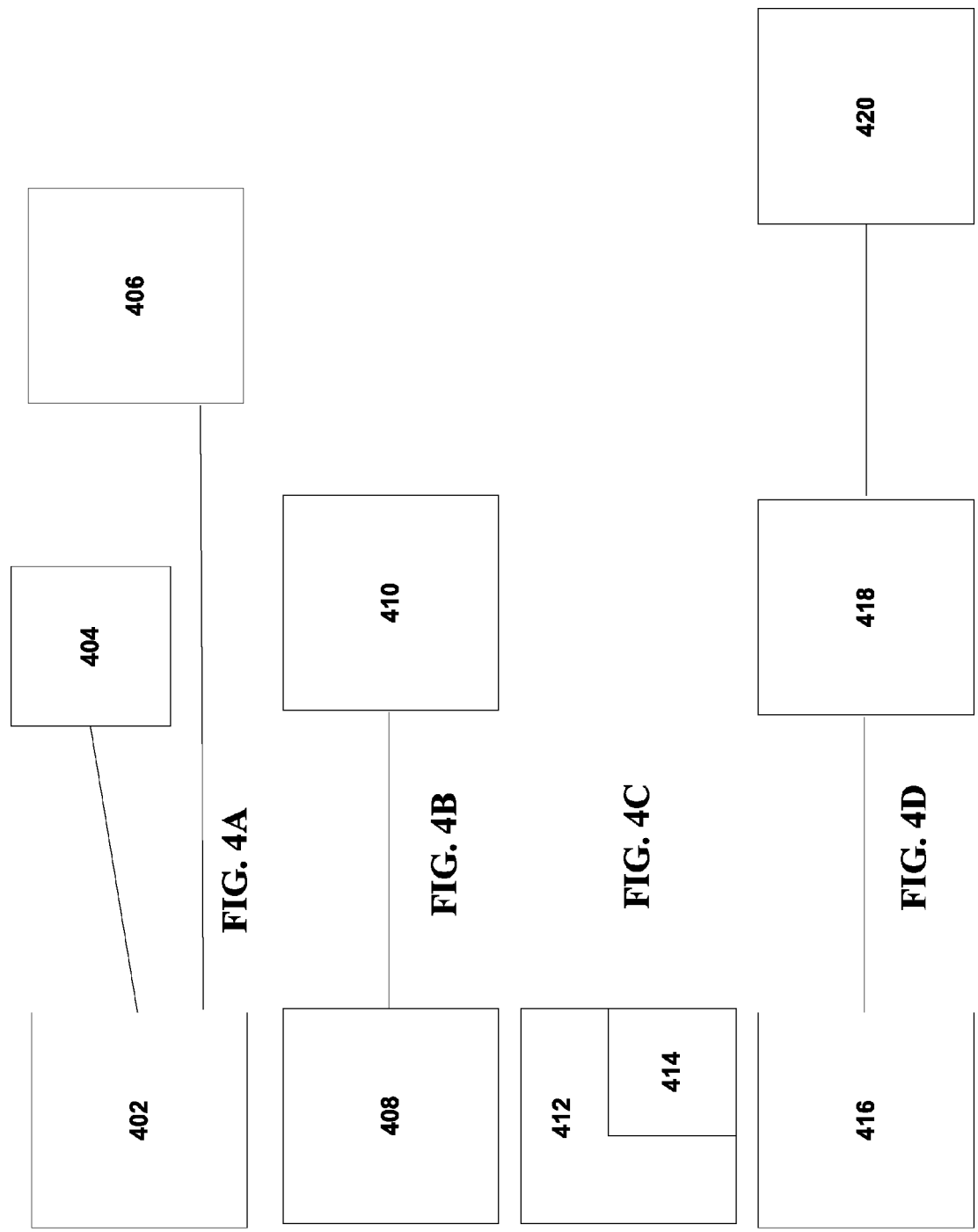
FIGS. 4A, 4B, 4C, and 4D depict examples of systems for quality control.

FIGS. 4A, 4B, 4C, and 4D are examples of QC systems. In FIG. 4A, a synthesizer 402 is communicatively coupled to a QC system 404 and a dispensing system 406. The QC system 404 and the dispensing system 406 are connected in parallel to the synthesizer 402.

In FIG. 4B, a synthesizer 408 is communicatively coupled to a QC system 410.

In FIG. 4C, a synthesizer 412 has an integrated QC system 414. The fluid paths of both the synthesizer 412 and the QC system 414 are desirably replaceable while the control systems for operating the synthesizer fluid path and the control system for directing the sample through the QC system and for interrogating the sample are desirably re-usable once new fluid paths are installed. The fluid paths are contemplated to include valving, reaction chambers, reagent supplies, fluid pump (or motive) means, and interrogation cells.

In FIG. 4D, a synthesizer 416 is communicatively coupled to a dispensing system 418 which is communicatively coupled to a QC system 420. The present invention contemplates that the QC system 420 may be either integral to the dispensing system or disconnectable or disconnectably attachable to the dispensing system.

In each of the preceding embodiments depicted in FIGS. 4A-D, the synthesizer may be a device which produces a radiopharmaceutical. For example, the synthesizer may be a GE FASTlab system. The QC system may be as described in FIG. 3 and other descriptions herein. The dispensing system is a device that dispenses doses into vials and/or syringes for storage and/or dosing to patients. For example, the dispensing system may be a system as shown and described in FIGS. 8 and 9 below. The communicative coupling between the individual components may be fluidic coupling and electronic coupling. The fluidic coupling may be through a manifold having one or more valves and pumps to move the fluid volume of a radiopharmaceutical through the manifold and into the vials and/or syringes. The electronic coupling may be in the form or interfaces or contacts enabling the exchange of data and signals between the components. Each of the components of FIG. 4 may be computer based, such as having one or more computer processors, or being computer-controlled.

Figure 5:
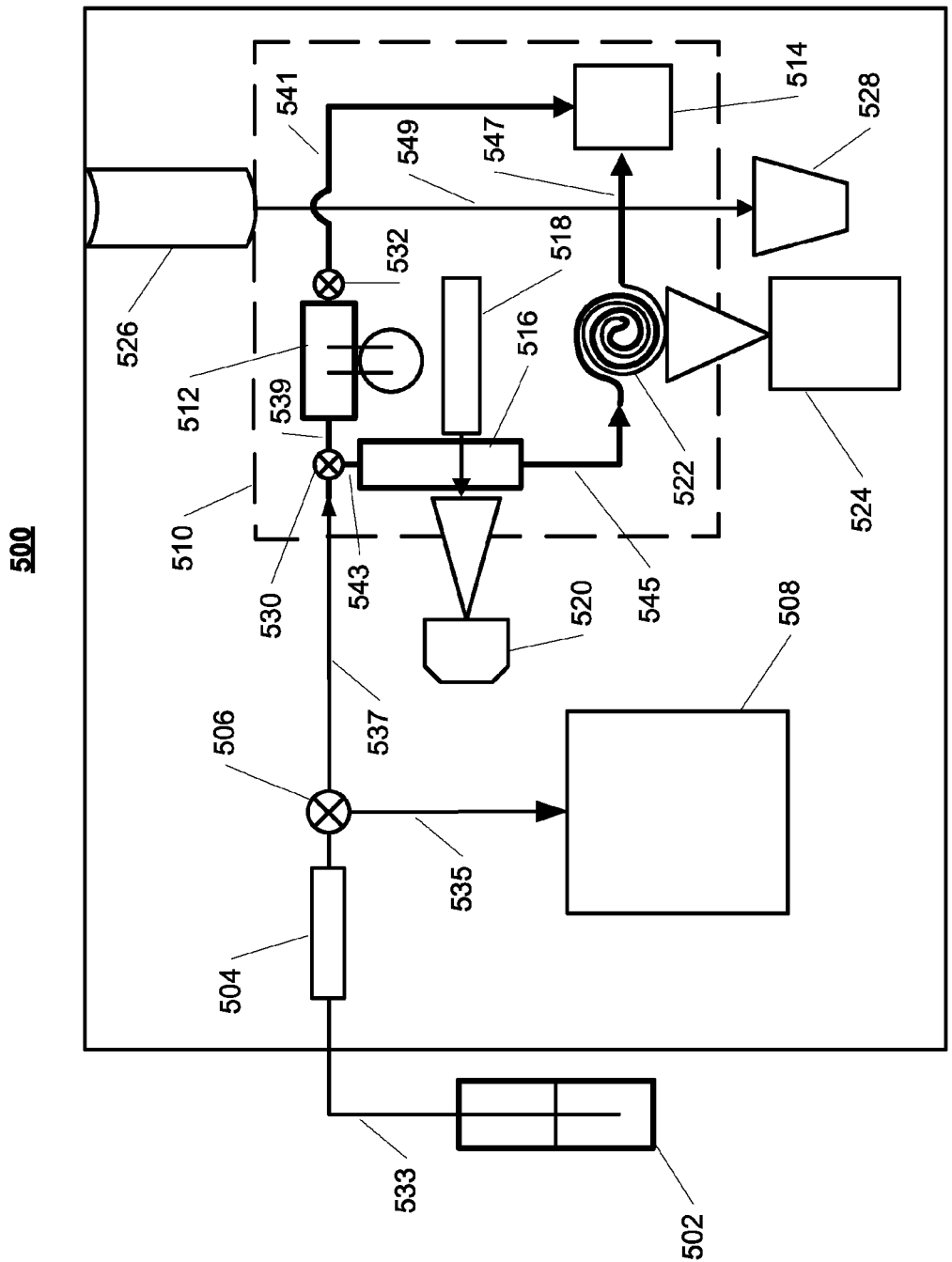
FIG. 5 depicts a quality control system according to an exemplary embodiment of the invention.

FIG. 5 depicts a quality control system according to an exemplary embodiment of the invention. The system 500 depicts a quality control ("QC") system according to exemplary embodiments. The system 500 may be an integrated or stand-alone QC system. For example, the system 500 may represent the quality control systems and components shown in FIG. 2, 3, or 4.

The system 500 may receive a sample input from a source 502. The sample input may be a fraction from the batch production of a radiotracer or radiopharmaceutical. Thus, for example, the fraction may be aliquoted in the source 502 from another source (e.g., the batch). According to some embodiments, the source 502 may be a vial from the synthesizer of a patient dose, that has been selected, randomly or otherwise, for QC testing. An optional pump 504 may be used to pump the fluid from the source 502 into the system through a fluid path 533, as well as apply motive force to the fluid. According to some embodiments, the pump 504 may be a syringe pump. It should be appreciated that other types of suitable pumps may be used. The fluid can also be "pumped" manually from the source 502 into the system 500, thus obviating the need for a the pump 504. Other motive means may be used to move the fluid into the system 500 such as gravity, capillary action, pressure (e.g., at the source), electrical potential, and vacuum (e.g., a vacuum applied at some point downstream from the source). It should be appreciated that the fluid pathways described are desirably transparent to allow for observation of the fluid and conducting the various QC tests on the fluid which may involve imaging the fluid and passing a light through the fluid.

An optional valve 506 (e.g., a membrane valve) may be present for routing of the sample fluid or head-space gas(es) to fluid path 535. According to exemplary embodiments, 50-150 μL of the sample taken from the source 502, may be diverted into a mass spectrometer (MS) 508, using the fluid path 535, for mass spectral analysis for an indication, e.g., that the desired radiopharmaceutical is present in the sample. Alternatively, a head-space gas sample may be introduced into system 500 and diverted by valve 506 to a HS-MS 508 for the determination of the presence and/or concentration of residual solvents (e.g., solvents used in the synthesis of the radiopharmaceutical). According to some embodiments, the HS-MS may be replaced with a GC device. The rest of the sample (e.g., 1 mL or less) may then be input into a cassette 510. The cassette 510 is preferably removable from the system 500 and is disposable.

It will be understood that since the pump 504 and the valve 506 are optional, they could both be present; the pump 504 may be present and the valve 506 may be absent; the valve 506 may be present and the syringe pump 504 may be absent; or the pump 504 and the valve 506 may be absent. If an HS-MS analysis is conducted (using sub-system 508), as described in greater detail below, at least the valve 506 may be present. External motive means may be used to direct a fluid towards and into the cassette 510. Other motive means, such as capillary action may be used for fluid movement.

Valves 530 and 532 route the sample or fractions thereof to the appropriate components. These valves, like valve 506, may be membrane valves or directional stopcocks. The valves 530 and 532 may further include pumps or motive means for routing of the sample through the cassette 510. The valves and pumps, for the system 500, are desirably constructed of a material such that the cassette 510 has no leakage. The material may be complementary to the disposable cassette material. The fluid enters the cassette 510 through the fluid path 537 which enters the valve 530 as shown.

For the HS-MS analysis, the sample may be heated to approximately 90-100° C. before the head-space gas sample is withdrawn from the head-space of the source 502 and introduced into the MS/HS-MS for quantification of the residual solvents. It should be appreciated that the source 502 may require sealing to contain the headspace gases produced during the heating period. The heating time may depend upon the sampling and detection procedure which is chosen. The MS should be able to acquire the mass spectrum for typical residual solvents that are relevant for the typical PET or SPECT radiopharmaceuticals, such as, ethanol, acetonitrile, methanol and others. The MS data may be used for direct quantification of the residual solvents, such as through integration of the solvent specific fragment intensity vs. time data and correlation to predetermined standard curves and response factors. This method may use standard reference solutions for calibration of the responses.

Within the cassette 510, a portion of the sample (e.g., 10-50 μL), is directed into a pH component 512 through the fluid path 539. Once the pH determination is complete, the sample amount used for this test is transferred to the waste reservoir or chamber 514 through the fluid path 541. A portion of the sample that entered the disposable cassette 510 is also directed by the valve 530 toward a visual testing component 516 through the fluid path 543. Once in the visual testing component 516, a light source 518 is used to illuminate the sample such that a camera 520 can acquire an image of the sample. A CCD camera or a complementary metallic oxide semiconductor ("CMOS") may be used to acquire the image. The image thus obtained is desirably analyzed using image recognition software. The camera may be a digital camera. The camera 520 is contemplated to be fixed within QC system 500 so as to be also reusable for successive cassettes 510.

A portion of the sample is then transferred, using fluid path 545 beyond the visual testing component 516 to a capillary electrophoresis ("CE") component 522. The shape of CE component may be manipulated so as to minimize the size of the cassette 510. According to exemplary embodiments, the CE component may be a miniaturized CE unit. A CE unit typically includes an elongate fluid path whose interior volume is filled with a separation gel/matrix. Alternatively, the interior volume of the fluid path is empty, and/or the interior surface of the fluid path may be coated to minimize fluid/surface interaction interferences to the fluid flow. The fluid path is contemplated to be defined between two overlying planar substrates as is known in the electrophoresis chip art. The present invention also contemplates that opposing ends of the CE unit fluid path each connected to elongate conduits for providing the sample to the CE unit and for carrying the sample from the sample reservoir to waste. In some embodiments, the CE fluid path may be 20 to 40 cm in length or even longer. Desirably, a gamma detector imager 524 is used to analyze the sample as it passes through the fluid path of the CE unit. The readings from the gamma detector imager 524 can be correlated to one or more of the location of the radiopharmaceutical and other compounds (e.g., impurities) in the fluid path; the concentration (relative and/or absolute) of the radiopharmaceutical and other compounds (e.g., impurities) in the sample; and RCP and RNP of the radiopharmaceutical. In such embodiments, the CE unit, in conjunction with the gamma detector imager 524 are the RCP and RNP component of the present invention.

In some embodiments, the CE component 522 is also a part of the chemical purity component because, as the sample travels through the CE unit, the sample's components are separated. The separated components are typically the desired radiopharmaceutical and any other compounds that may be present as contaminants (e.g., starting materials) but which will travel through the CE unit at different speeds than the radiopharmaceutical. The presence or absence of contaminants is an indication of the level of purity of the sample.

After the sample travels through the CE component 522, in some embodiments, the sample passes by a detector assembly 528 using the fluid path 547, the data from which detector may be used to determine the relative (or absolute) amounts of desired radiopharmaceutical and contaminants, if present, that are present in the sample. In some embodiments, the detector assembly 528 is part of a chemical purity component. In some embodiments, the detector assembly 528 is a UV detector assembly. Such a UV detector assembly includes a UV source 526 that emits a signal that passes through the fluid path of the sample as it travels past the detector assembly 528 as shown by the line 549. Changes in the optical density (OD) of the sample are detected by measuring the signal from the UV source 526 by a detector, e.g., photo-diode array detector, within the detector assembly. The UV source may emit a light source of 200-320 nm. The UV light may be used to detect organic components in the sample fraction in real time.

According to some embodiments, capillary electrochromatography ("CEC") may be used in place of CE. CEC provides an alternative to CE, which may provide a more miniaturized component for the cassette. CEC functions in a similar manner to CE. CEC may also provide an alternative to liquid chromatography (LC). CEC devices are commercially available (Agilent Technologies, Foster City, Calif.) and such commercial devices may be integrated into the exemplary embodiments as described herein.

Finally, the sample is transferred to the waste chamber 514. The sample has now had the requisite QC checks performed thereon. The cassette 510 may be removed from the system 500 and disposed of. It should be understood that the system 500 may have appropriate shielding installed to prevent radiation exposure during the QC process using the system. The cassette 510 desirably includes appropriate shielding to prevent radiation exposure during handling of the cassette 510 when it contains a sample when it is removed from the system 500. The present invention further contemplates that shielding may be provided about only those portions of cassette 510 exhibiting the highest levels of radioactivity post-usage. For example, cassette 510 may accept a lead shield over or about waste receptacle 514 and/or the fluid path of the CE component 522. In some embodiments, the QC system may contain shielding including shielding over the measurement components and shielding to protect operators from radiation exposure. A new or fresh cassette may be inserted into the system 500 following completion of the analysis so that another sample may be analyzed.

The cassette 510 may include the pump 504, the valve 506, and flow path 535 (in addition to the other components and fluid paths shown to be a part of the cassette 510 in FIG. 5). By including these structures in the cassette 510, contamination of the system 500 may be minimized or avoided to limit or eliminate cleaning and purging requirements to prevent cross contamination because the sample fluid is confined to the cassette structure and only the testing sources and sensors are external, but do not directly need to contact the sample fluid.

According to some embodiments, a sample may be input onto the disposable cassette 510 before the cassette is inserted into the system 500 for analysis. If an HS-MS or GC analysis is conducted, the sample would be distributed from the disposable cassette 510 to the HS-MS 508. A pump 504 may be used as previously described to, e.g., draw at least a portion of the sample from the cassette 510 to accomplish this testing.

It should be understood that more or less QC tests may be performed using the system 500. For example, components could be added or removed from that described above. Also, even if several test components are present on the cassette, not all of the test need to be run. The tests, sample amounts, and sample flow path are meant to be exemplary and non-limiting.

Furthermore, the system 500 may be computer implemented such that the system 500 includes one or more computer processors, power sources, computer memory, and software. The system 500 may be communicatively coupled to one or more external computing systems. For example, the system 500 may be communicatively coupled through a computer network, either wired or wireless or a combination of both, to an external computer system. The external computer system may provide commands to cause the system 500 to operate as well as collect and analyze data from the QC tests. This computer hardware and software may enable to the system 500 to automatically operate and to perform the QC tests, to collect data from the QC tests, and to analyze the data. Finally, the computer hardware and software may support the system 500 producing an output report with the results of the QC tests. The output report may be output electronically and/or in a hard copy format. The system 500 may have one or more input devices and display devices associated therewith.

Figure 6:
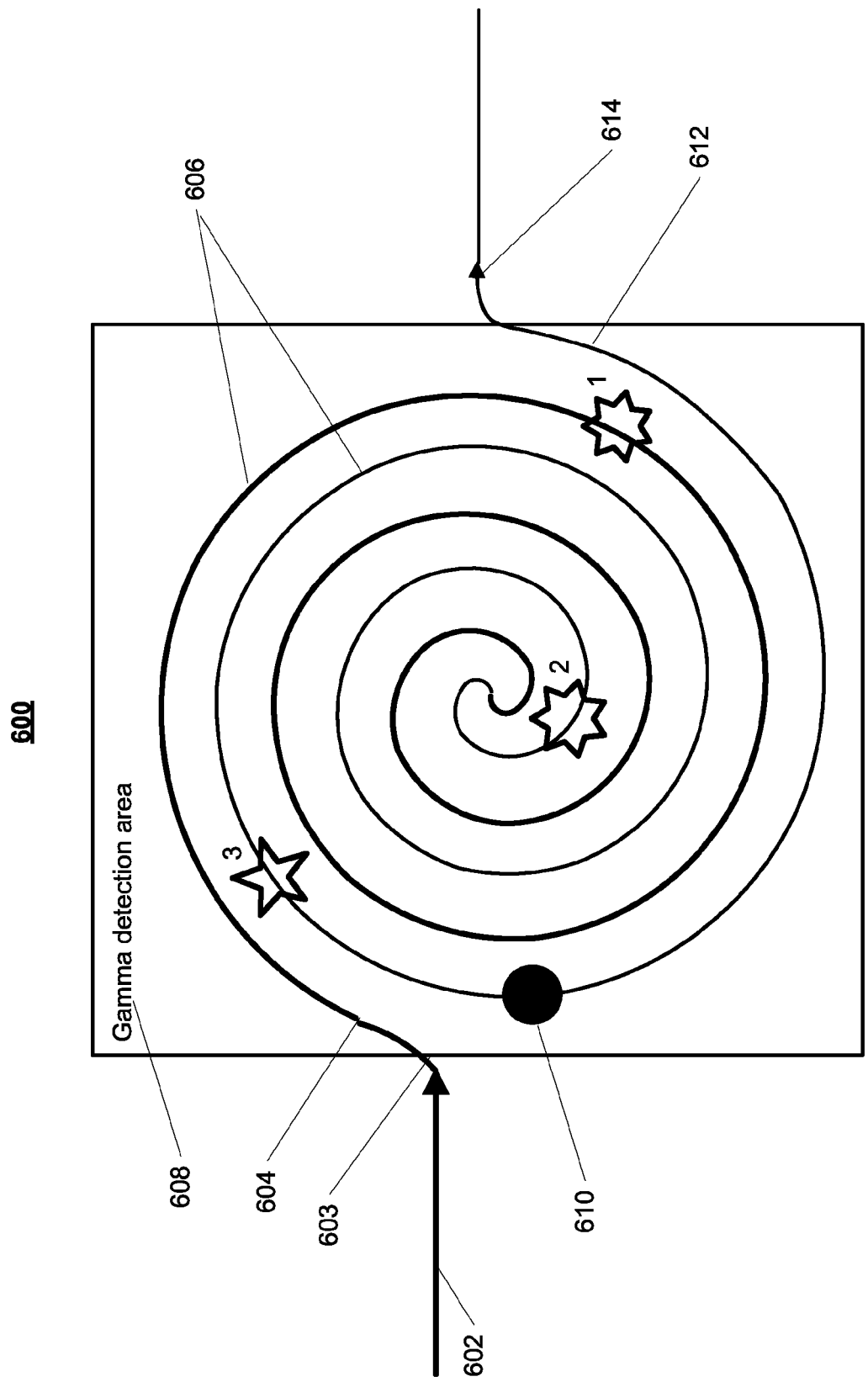
FIG. 6 depicts a capillary electrophoresis and gamma radiation detection component according to an exemplary embodiment of the invention.

FIG. 6 depicts a CE and gamma radiation detection component according to exemplary embodiments. The CE component 600 may be used as part of the QC system 500 depicted in FIG. 5. The CE component 600 may provide a two dimensional method of gamma ray imaging and/or spectroscopic detection which allows simultaneous determination of the location of radioactive compounds within the component and the concentration of each radioactive compound. The component also allows for the verification of RCP and RNP, as described briefly above. Gamma ray imaging (e.g., an imaging plate detector) is non-specific to different radioisotopes and hence is applicable to RCP and radioactive concentration. Gamma ray spectroscopic detection (e.g., spectrometer) is used to identify different radioisotopes for RNP. A sample is introduced (e.g., pumped) via an inlet 602 into the fluid path 603 of the CE component 600. Since radiopharmaceuticals may be non-ionic, in some embodiments, a universal buffer system that will allow separation of such non-ionic molecules based on a system of polar solvents and or varying of the pH of the buffers may be used. In some embodiments, the fluid path 603 (e.g., capillary column) includes a separation gel/matrix and the radiopharmaceutical is separated from impurities over the length of the capillary. In some embodiments, the gel/matrix starts at 604 (i.e., the portion of the fluid path 603 adjacent to the inlet 602). The gel/matrix or polar solvent may be present in the fluid path 603 prior the sample entering. In some embodiments, the solvent may be stored externally to the fluid path 603 and ported into the capillary prior to entry of the sample fluid. Solvent mixing may be required prior to usage. The solvent may be either aqueous or organic. For example, the solvent may be acetonitrile or methanol or a mixture thereof. In some embodiments, it may be necessary to combine the sample, prior to introduction via inlet 602, with an ionic agent, preferably a quaternary ammonium salt (e.g., tetrahexylammonium or tetraheptylammonium), as described in J. S. Fritz, *Electrophoresis* 24: 1530-1536 (2003) and W. Ding and J. S. Fritz, *Anal. Chem.* 69: 1593-1597 (1997), both of which are incorporated by reference as if fully set forth herein.

Figure 7:
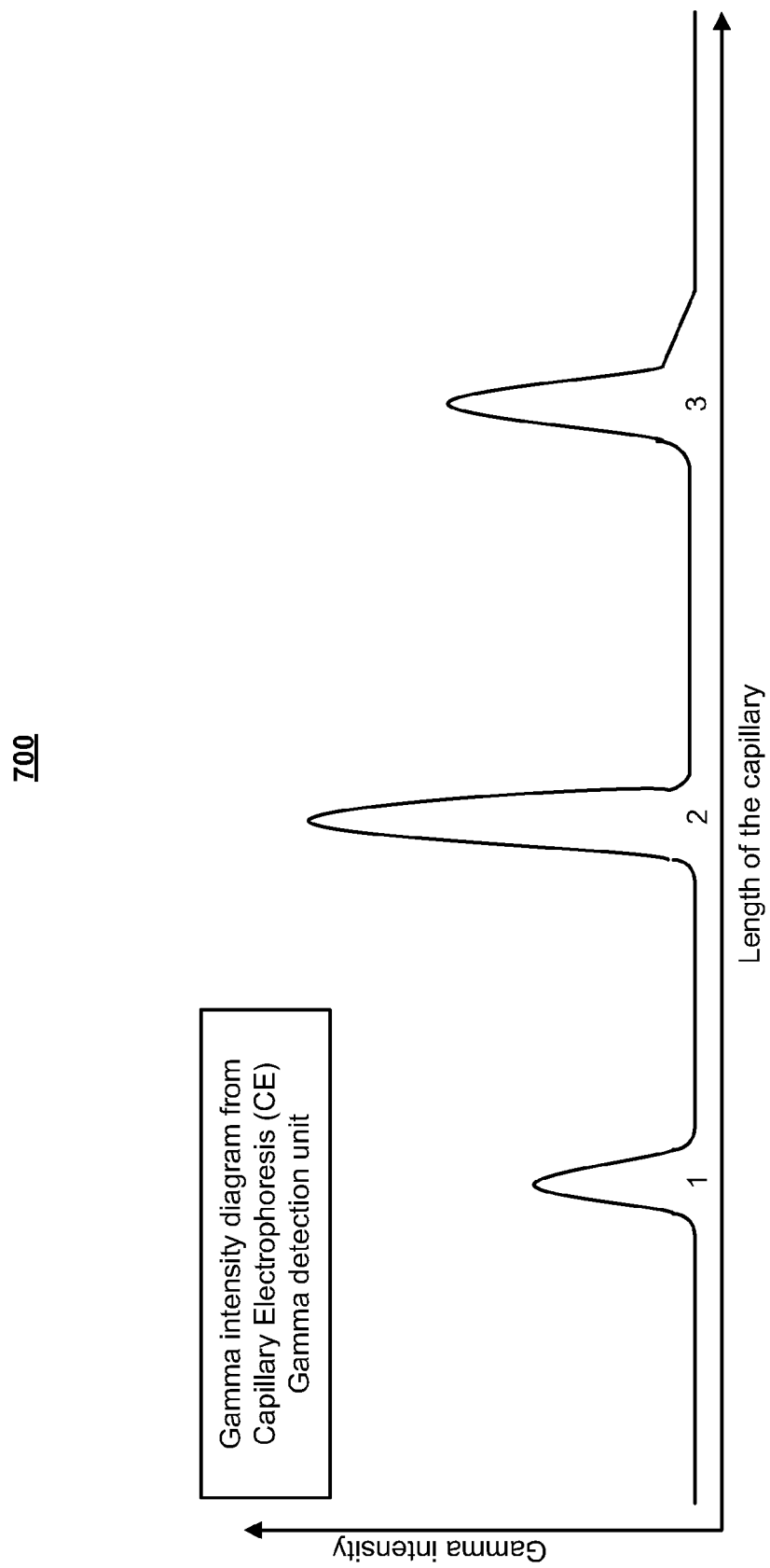
FIG. 7 depicts an example of linear graph output of gamma detection from the capillary electrophoresis and gamma radiation detection component according to an exemplary embodiment of the invention.

When the sample enters the fluid path 603, electrical potential is applied to the fluid path so as to cause a current to flow along its length. In some embodiments, the fluid path 603 is double coiled as shown at 606, thereby increasing the length of the column and thus the separation resolution of the column. In addition, the double coiling 606 of the fluid path 603 enables the use of a minimum number of gamma detection units in order to acquire a gamma image of the fluid path 603 in the gamma detection area 608. The gamma image may be interpreted by software and show it in a linear graph and determine the sizes of the radioactive entities (e.g., the radiopharmaceutical). FIG. 7 depicts an exemplary trace 700 from the component depicted in FIG. 6. On the trace 700, three positions are indicated, labeled as "1", "2", and "3" which correspond to the same labeled positions in FIG. 6.

In some embodiments, during the CE process, a critical point 610 is continuously monitored and will stop the current when radioactivity is detected. The critical point 610 is a predetermined point located close to but not at the end in the fluid path 603. When the first radioactivity is observed at the critical point 610, it is known that the sample has at least reached that point. The system may then trigger a stop-signal to ensure that the sample does move too far in the fluid path 603 or out of the fluid path 603. The gamma detector/spectrometer array may then process the data and determine the RCP of the sample, verify the RNP and the intensity of the radiation, thus allowing the QC system to calculate the recommended dose for injection into the patients. In other embodiments, once the image is processed, the current will be reapplied and the fractions of the sample may leave the column at 614. The gel/matrix may terminate at 612. According to exemplary, embodiment, each component of the sample may then sequentially flow past a detector assembly, such as the UV detector assembly 528 shown in FIG. 5 above. It is at this point that the chemical purity of the sample can be assessed as described above in the context of FIG. 5.

Figure 8:
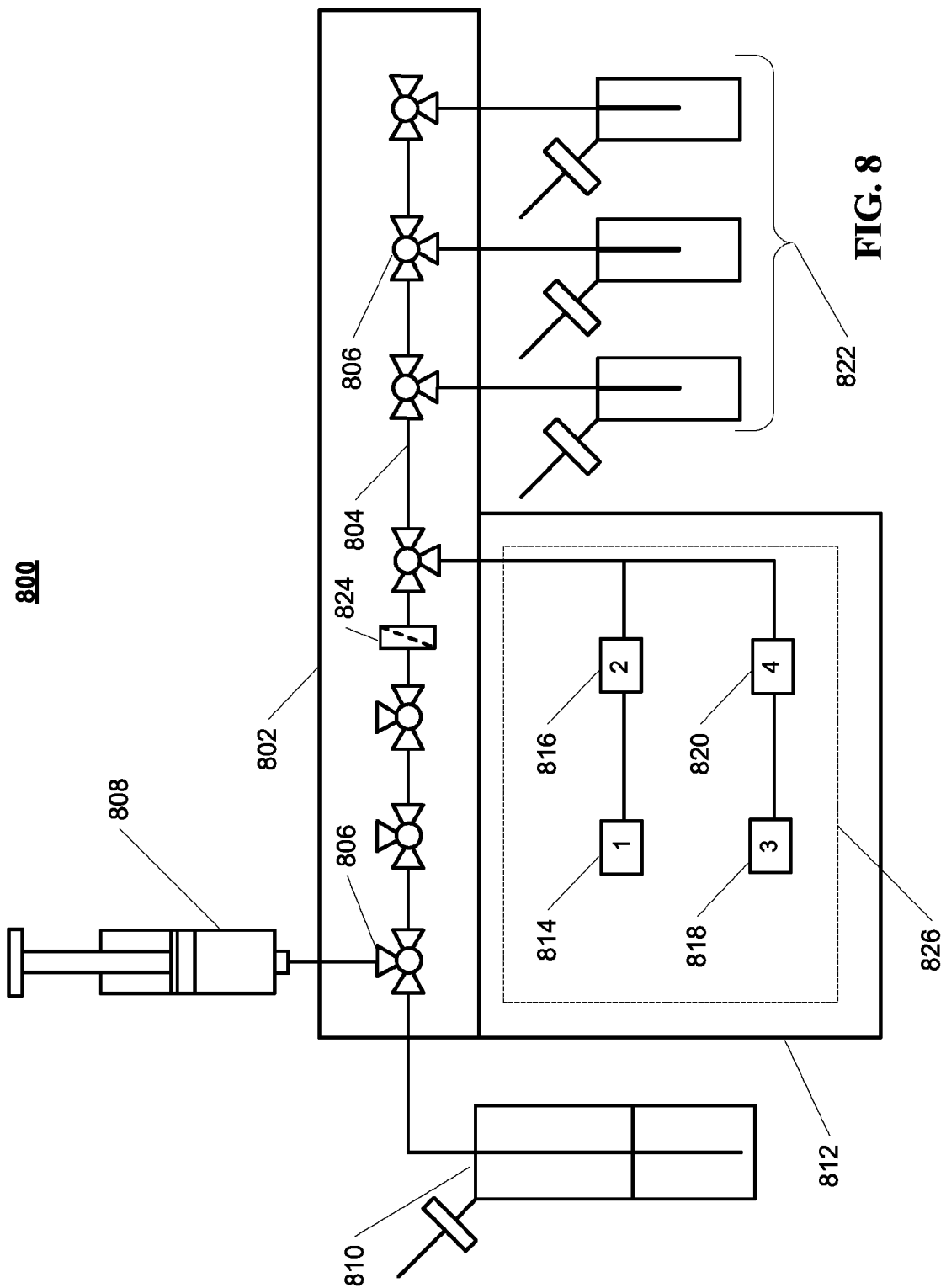
FIG. 8 depicts a manifold system for dispensing a radiopharmaceutical connected to a quality control system according to an exemplary embodiment of the invention.

FIG. 8 depicts a manifold system for dispensing a radiopharmaceutical connected to a quality control system according to an exemplary embodiment of the invention. System 800 may be integrated with a synthesizer for radiopharmaceuticals such that the system 800 is internal to the synthesizer (not shown). In other embodiments, the system 800 may be coupled to, or otherwise connected to the synthesizer so as to directly receive the output from the synthesizer for both dispensing and aliquoting a sample to a QC component for QC testing. The system 800 includes a dispensing sub-system 802. The dispensing sub-system 802 desirably includes a manifold 804 for distribution of a fluid. According to exemplary embodiments, the fluid is a radiopharmaceutical. The manifold 804 desirably includes a series of valves 806 having selectable configurations so as to control the distribution of the fluid. The valves 806 may be multi-position valves such as 2 or 3 way valves. The valves 806 may be manual stopcock-type valves, or may be electronically-actuated valves or electromechanically-actuated stopcock valves.

The system 800 includes a syringe pump 808 (other fluid motive means such as pump means) connected to the manifold 804 through a valve 806. The syringe pump 808 functions as understood by one of ordinary skill in the art, through reciprocal motion of the syringe plunger and the coordinated of the valve 806 so as to alternately provide for drawing of a fluid from the vial 810 into the syringe pump 808 and then back through the valve 806 through the manifold 804. For example, the syringe pump 808 draws a vacuum and intakes a predetermined amount of fluid from the manifold 804. The fluid is sourced from a feed vial 810. The feed vial 810 is filled with fluid from the synthesizer. The feed vial 810 contains the required amount of fluid for the QC system. In other embodiments, the feed vial 810 may be an output container for the synthesizer and may contain an amount of fluid required for QC testing and for dispensing. According to some embodiments, the fluid may be sourced directly from an output of the synthesizer. The syringe pump 808 exhausts the fluid into the manifold 804 causing it to flow through the manifold and be routed according to the configuration of the valves 806. The sampling of the fluid may be automatic or manual. For example, the system 800 may automatically configure the manifold 804 for dispensing the fluid for QC testing. In other embodiments, a manual configuration may be required and a manual sample may be used.

A QC system 812 is contemplated to be present in the system 800. The QC system 812 desirably provides functionality to perform one or more QC tests on the fluid. As depicted in the system 800, the QC system 812 may have four components for QC testing: 814, 816, 818, and 820. According to exemplary embodiments, these components may be capable of performing particular QC tests on the fluid. It should be noted that the configuration shown is exemplary and meant to be non-limiting, as more or less than four components may be used. The QC system 812 is contemplated to either perform the analysis, measurements and calculations automatically using a computerized system or to be scanned by a computerized system which will then perform the analysis and the final results and conclusions are summarized in a final report for each analysis. The QC results may be output in an appropriate format, such as hard copy and/or electronically. According to some embodiments, the QC system 812 includes a disposable cassette 826 containing the QC components as described herein.

The fluid not sampled is dispensed for further use into the vials 822. While three vials are shown, it should be understood that more or less vials may be connected to the dispensing sub-system 802 for dispensing of the fluid. Further, the manifold 804 has an optional filter 824 to remove material or impurities from the fluid drawn from, e.g., the feed vial 810. While a single filter 824 is shown, additional filters may also be included.

It should be appreciated that cleaning or purging of the dispensing sub-system 802, may be required to prevent contamination of subsequent fluids using the dispensing sub-system. Appropriate cleaning solvents, devices, and procedures may be included as part of the system 800. According to exemplary embodiments, the cleaning procedure may be automatically performed following a use of the system 800. According to exemplary embodiments, the manifold sub-system 802, and the cassette 826, may be disposable such that these components may be removed and disposed of following use. In some embodiments, other portions of the system 800 may be removable and/or disposable, such as the QC system 812 and the syringe pump 808.

Figure 9:
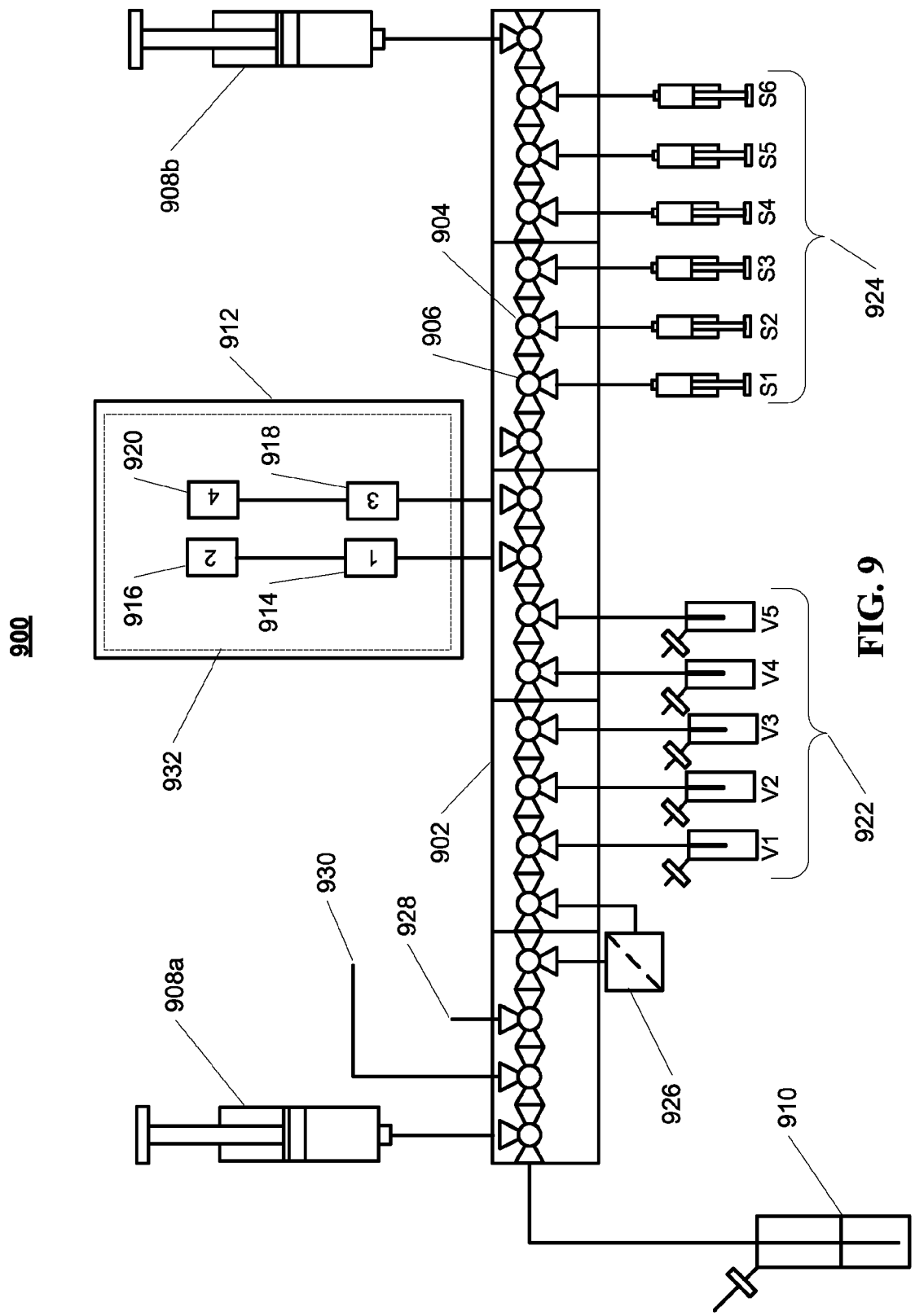
FIG. 9 depicts a manifold system for dispensing a radiopharmaceutical connected to a quality control system according to an exemplary embodiment of the invention.

FIG. 9 depicts a manifold system for dispensing a radiopharmaceutical connected to a quality control system according to an exemplary embodiment of the invention. As seen in FIG. 9, the system 900 may be similar in configuration to the system 800 depicted in FIG. 8, but on a larger scale. System 900 may be integrated with a synthesizer such that the system 900 is internal to a synthesizer (not shown). In other embodiments, the system 900 may be coupled to or otherwise connected to the synthesizer. The system 900 may include a dispensing sub-system 902. The dispensing sub-system 902 may consist of a manifold 904 for distribution of a fluid. According to exemplary embodiments, the fluid may be a radiopharmaceutical. The manifold 904 may have a series of valves 906 to control the distribution of the fluid. The valves 906 may be multi-position valves such as 2 or 3 way valves. The valves 906 may be manual stopcock-type valves or may be electronically-actuated valves, or electromechanically-actuated stopcock valves.

Syringe pumps 908a and 908b may be connected to the manifold 904 through a valve 906. The syringe pumps 908a and b may function as understood by one of ordinary skill in the art. According to exemplary embodiments, two syringe pumps, 908a and 908b may be used. The syringe pumps 908 may operate in tandem or in series. The fluid may be sourced from a feed vial 910. The feed vial 910 may be filled with fluid from the synthesizer. The feed vial 910 may contain a required amount of fluid for the QC system. For example, the syringe pump 908a may draw a vacuum and intake a predetermined amount of fluid into the manifold 904 from the feed vial 910. In other embodiments, the feed vial 910 may be an output container from a synthesizer and may contain an amount of fluid drawn therefrom as required for QC testing and for dispensing. According to some embodiments, the fluid may be sourced directly from an output of the synthesizer. The syringe pump then 908a exhausts the fluid into the manifold causing it to flow through the manifold and be routed according to the configuration of the valves 906. The sampling of the fluid may be automatic or manual. For example, the system 900 may automatically configure the manifold 904 for dispensing the fluid for QC testing. In other embodiments, manual operation may be required and a manually-drawn sample may be used.

A QC system 912 is desirably incorporated into the system 900. The QC system 912 desirably includes functionality to perform one or more QC tests on the fluid. As depicted in the system 900, the QC system 912 may have four components for QC testing: 914, 916, 918, and 920. According to exemplary embodiments, these components may be capable of performing particular QC tests on the fluid. It should be noted that the configuration shown is exemplary and meant to be non-limiting, as more or less than four components may be provided. The QC system 912 may either perform the analysis, measurements and calculations automatically itself using a computerized system or provide interrogation cells to be interrogated by separately provided interrogation devices and the final results and conclusions are summarized in a final report for each analysis. The QC results may be output in an appropriate format, such as hard copy and/or electronically. According to some embodiments, the QC system 912 may desirably include a disposable cassette 932 containing the QC components as described herein.

The fluid is be dispensed for further use, following the QC testing for example, into the vials 922 and/or syringes 924. While five vials and six syringes are shown, it should be understood that more or less vials and syringes may be connected to the dispensing sub-system 902 for dispensing of the fluid. Further, the manifold 904 may include an optional filter 926 to remove material or impurities from the fluid drawn, e.g., from the feed vial 910. While a single filter 926 is shown, additional filters may be included. Manifold venting may be available through a port 928 supporting a venting filter (not shown). Further, a connection 930 may be provided for an integrated automated or manual filter testing unit.

It should be appreciated that cleaning or purging of the dispensing sub-system 902, may be required to prevent contamination of subsequent fluids using the system 900. Appropriate cleaning solvents, devices, and procedures may be included as part of the system 900. According to exemplary embodiments, the cleaning procedure may be automatically performed following a use of the system 900. According to exemplary embodiments, the manifold sub-system 902, and the cassette 932, may be disposable such that these components may be removed and disposed of following use. In some embodiments, other portions of the system 900 may be removable and/or disposable, such as the QC system 912 and the syringe pumps 908a and 908b.

Figure 10:
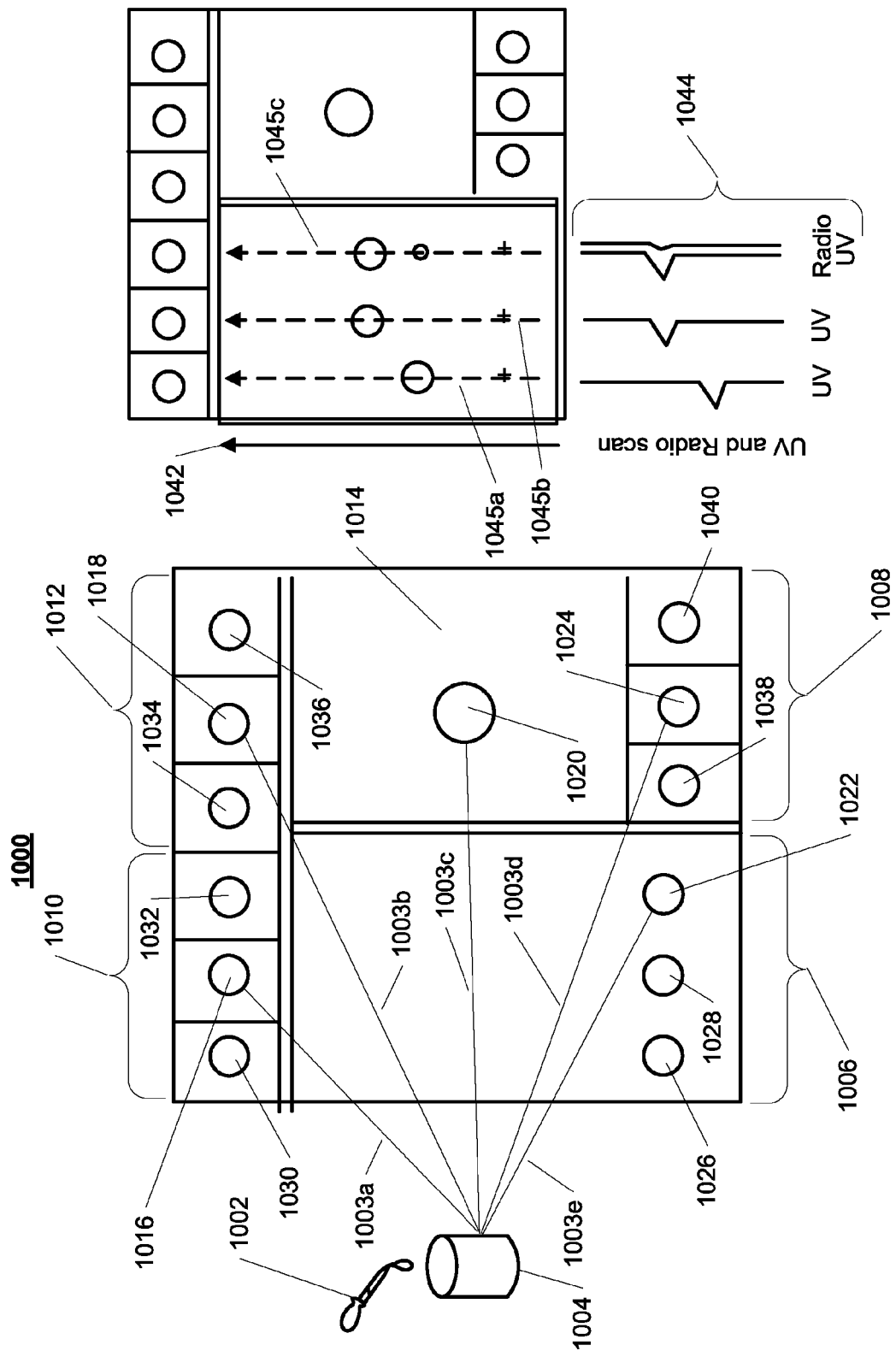
FIG. 10A depicts a cassette for performing quality control testing according to an exemplary embodiment of the invention.
FIG. 10B depicts the performance of a quality control test using the cassette of FIG. 10A according to an exemplary embodiment of the invention.

FIG. 10A depicts a cassette 1000. The cassette 1000 may be a disposable cassette as described herein. The cassette 1000 is desirably configured with a number of components for QC testing. Each component performs a different test. As should be appreciated, a plurality of configurations are possible. The cassette 1000 is configured to permit reading of certain results on the cassette itself. For example, areas where one or more references may be located on the cassette and areas where the sample may be introduced are provided on the cassette. According to some embodiments, the results from the QC tests may be electronically read and output by a computer based system. For example, the cassette 1000 may be used in a QC system, as described herein, such that the tests are automatically conducted, the data is automatically analyzed, and the results are automatically output. Each cassette 1000 may be configured for use with a particular radiopharmaceutical.

A sample 1002 of a radiopharmaceutical is applied to the cassette 1000. The sample 1002 may be a fluid. The sample may be applied using a number of methods known in the art. For example, the sample 1002 may be applied via injection using a syringe, such as a microliter syringe, through a dropper, or through a manifold connection from a synthesizer or a dispensing system, such as the systems described above in FIGS. 8 and 9. Other inputs may be used to apply the sample 1002. The sample input may be automated or manually performed. A specific quantity of the sample 1002 may be applied to the cassette 1000. A sufficient amount is required to support performance of each of the QC tests supported by the cassette 1000. The sample 1002 may be applied to or input to the cassette 1000 at an intake reservoir 1004. The intake reservoir 1004 may be a container for the fluid volume of the sample 1002. The intake reservoir 1004 may perform distribution and routing of the fluid volume of the sample 1002 to the various testing components of the cassette 1000 via, e.g., microfluidic flow paths. The intake reservoir 1004 may have one or more valves and/or pumps to support distribution of the sample 1002. The intake reservoir 1004 may perform automatic distribution of the sample 1002. The intake reservoir 1004 may be configurable to support distribution of the sample 1004 to a sub-set of the available QC testing components on the cassette 1000. For example, as shown in FIG. 10A, the intake reservoir 1004 distributes the sample to five sample input locations (e.g., 1016, 1018, 1020, 1022, and 1024) on the cassette 1000 via fluid paths 1003*a-e* with each location representing a component.

The cassette 1000 includes five components, 1006, 1008, 1010, 1012, and 1014, located thereon. The five components are desirably QC testing components. By way of exemplary non-limiting example, the components represent the following tests: component 1006 is a RCP test; component 1008 is a LAL test; component 1010 is a pH test; component 1012 is a K222 test; and component 1014 is a visual appearance test. It should be appreciated that other tests and combinations thereof are possible. Further, the layout of the components in FIG. 10A is exemplary only and other arrangements are possible.

Each of the components has a sample input location. The sample input locations are 1016, 1018, 1020, 1022, and 1024 as can be seen in FIG. 10A. In some embodiments, component 1006 includes a pre-loaded "cold" (i.e., non-radioactive) impurity reference sample 1026 and a "cold" reference sample 1028 (e.g., the "cold" version of the radiopharmaceutical). The present invention contemplates that the reference samples may be introduced into the cassette when it is manufactured; can be introduced by the user prior to inserting the cassette into the QC system; or can be introduced by the user after inserting the cassette into the QC system. These reference samples enable a comparison of the "hot" or actual sample to the references to determine if the sample contains one or more impurities. In addition, the references can serve as concentration references and/or calibration references for the QC system. For example, if the concentration of the cold reference sample 1028 and/or the concentration of the "cold" impurity reference 1026 is known, the intensity of any signal (e.g., a UV signal) read from their respective "lanes" 1045*a-b* can be correlated to each compound's concentration. The intensity of any signal read from the sample lane 1045*c* can then be correlated to the concentration of the respective compounds in the sample lane and, in turn, in the sample. Alternatively, or concurrently, the intensity of any signal read from lanes 1045*a-b* can be used to calibrate the QC system.

These reference samples are used in conducting the RCP test described in FIG. 10B. FIG. 10B shows an RCP test being conducted. The QC component 1006 includes a chromatography surface (e.g., a gel electrophoresis surface, thin-layer chromatography using silica gel or, in some embodiments, C-18-derivatized silica) having a UV-indicator. A suitable solvent is applied to the chromatography surface and is allowed to migrate via capillary action through the chromatography surface. As the solvent moves, it carries with it the "cold" impurity reference sample 1026 and the "cold" reference sample 1028 in their respective "lanes" 1045*a-b*. The solvent also carries with it the sample 1022 in its respective "lane" 1045*c* The progress of each sample can be monitored by a UV detector. The progress of the sample 1022, which includes radioactive material, can also be monitored using a gamma detector. Arrow 1042 depicts the migration of the ions from inputs 1022, 1026, and 1028 during the test. At 1044, exemplary results are depicted.

In component 1008, the hot sample at 1024 is compared to two reference locations, 1038 and 1040. According to exemplary embodiments, for the LAL test at component 1008, these locations may be wells or reaction tubes with LAL reagents at different levels (e.g., Charles River Laboratories PTS Cartridges, Wilmington, Mass.). Likewise in components 1010 and 1012, reference locations are provided. For example, in component 1010, the reference locations are 1030 and 1032. According to exemplary embodiments, these locations may be pH buffer solutions with a pH at a lower and a higher value (one value in either of the locations) of the acceptable pH range. A pH indicator may be in the form of a liquid solvent to be added or already present as an indicator gel in the location or a pH sensitive window. In component 1012, the reference locations are 1034 and 1036. According to exemplary embodiments, an indicator for determination of K222 may be included, such as, for example, silica gel substrate with iodoplatinate reagent. One location may be a blank and the other location may represent an upper limit value for K222. In component 1014, one sample location 1020 may be provided. This sample may be imaged using a CCD or CMOS device for visual comparison. Software may perform the comparison. Alternatively, a reference image may be provided for comparison.

According to some embodiments, the pH testing may be performed using UV/Vis-spectrophotometry. This test uses colored pH indicators where UV/Vis absorbance can be correlated to sample pH. A typical pH range for this testing is 5-9. The sample location 1016 may contain an indicator and/or other reagents which mix with the sample volume and enable the performance of this testing. The measurement testing is performed directly in the sample location. Some radiopharmaceuticals may contain inherent components such that no mixing is required to perform the pH testing in this manner. The present invention also contemplates that the comparison of the hot sample to the reference standards allows for the QC system to simultaneously be calibrated while making the comparisons. While other QC systems would require calibration of the interrogation devices used to detect the signals from the hot sample and cold references, the present invention allows for the detected signals to be calibrated according to the known reference standards.

According to alternative embodiments, the cassette 1000 may contain different configurations of QC components as described above. For example, the pH component (i.e., component 1010), may be replaced with a combination oxygen/pH testing component. Other components, such as the LAL component (i.e., component 1008) or the K222 component (i.e., component 1012) may one or both be replaced with an oxygen (dissolved and gaseous) component and/or a $CO_2$ testing component. These types of components include sensors which, in some cases, are commercially available. For example, sensors from PreSens may be integrated into the cassette 1000 for these components to conduct the appropriate tests. Other types of sensors are available and known in the art.

It should be understood that the configurations described for the cassette 1000 are equally applicable to the cassette 202 described above and vice versa.

Figure 11:
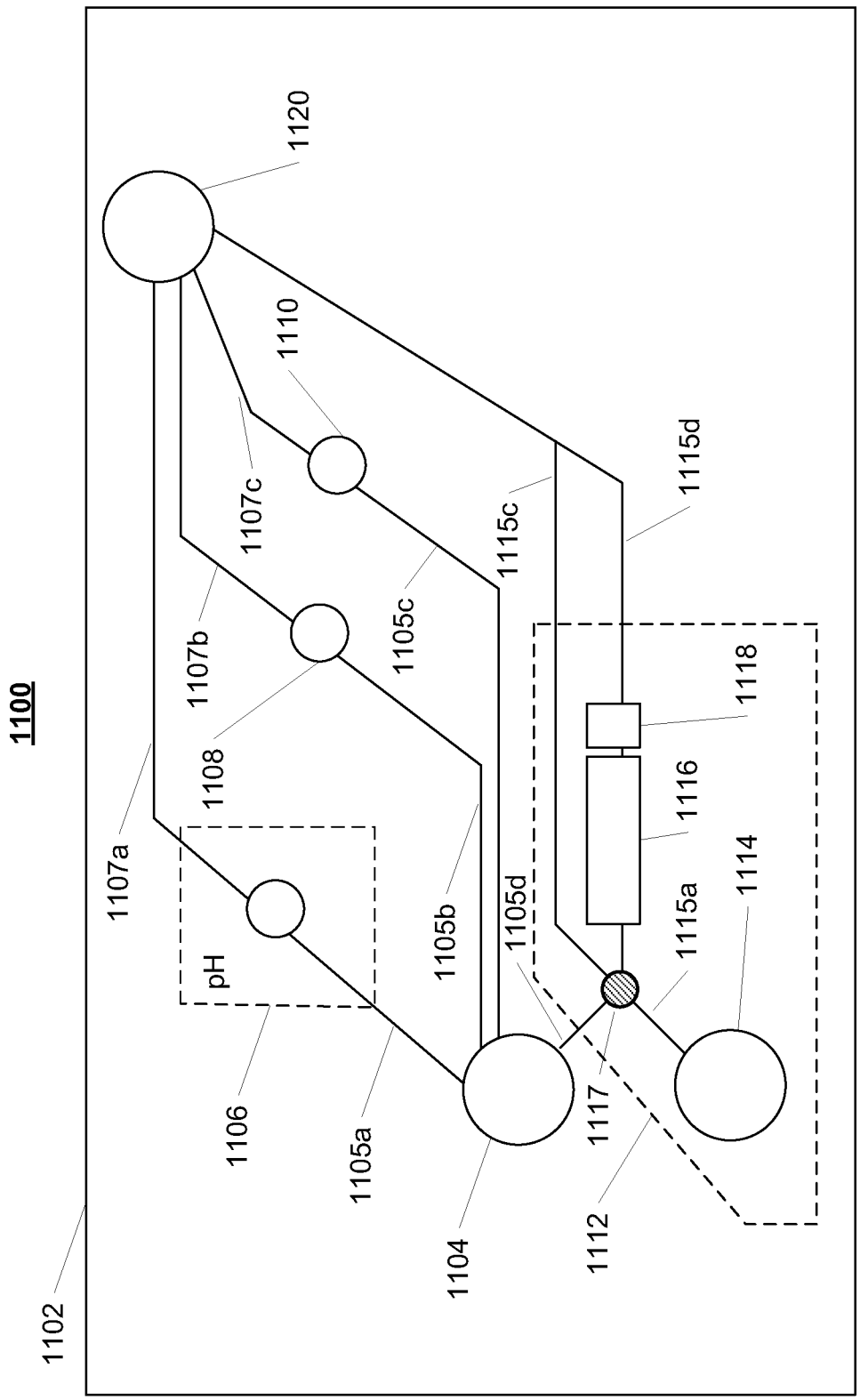
FIG. 11 depicts a cassette for performing quality control testing according an exemplary embodiment.

FIG. 11 depicts a QC testing cassette 1102 according to an exemplary embodiment of the invention. A QC system 1100 has a cassette 1102 for performing QC tests with the cassette 1102. The cassette 1102 may be configured to interface with a QC system as also described herein. The cassette 1102 may be configured to perform certain QC tests on a sample of a radiopharmaceutical. The cassette may have components or sensors contained thereon supporting these QC tests or for actually performing the tests. The tests are desirably performed automatically using the cassette 1102 when interfaced with a QC system. The testing may be controlled by one or more computer processors associated with the QC system as described herein. The QC system may collect data, analyze results, and perform reporting of the testing results. The cassette 1102 may be disposable and may have appropriate shielding to prevent or minimize radiation exposure. According to some embodiments, the cassette, by way of non-limiting example, may have dimensions of 10 cm×10 cm×5 mm. It should be understood that the configuration of the cassette 1102 is exemplary and meant to be non-limiting.

The cassette 1102 includes a microchip-type structure wherein two elongate planar substrates are brought together to define an elongate fluid path therebetween. The upper substrate defines a sample reservoir or inlet port 1104 in fluid communication with a fluid path. The sample reservoir 1104 may be a container into which a predetermined fluid volume of sample is input. The input of the sample may be manually or automatically performed. The sample reservoir 1104 may be fluidically coupled to the various testing components contained on the cassette 1102 such as through microfluidic pathways 1105a-d. Motive input to the fluid may be performed using one or more pumps and/or valves.

Component 1106 is a pH testing reservoir. The sample is routed to the component 1106 through pathway 1105a. The pH testing may be performed using a sensor or other pH testing methodology as described herein. The pH testing may be combined with oxygen testing as described herein. According to some embodiments, the pH testing may be done using an indicator (e.g., bromthymol blue) that changes color when the sample arrives at the pH testing component. The change in color may be detected visually or, in a preferred embodiment, spectrophotometrically using a micro UV-Vis spectrophotometer (UV-Vis light source and detector). This spectrophotometer may be a part of the QC system into which the cassette 1102 is inserted. In other embodiments, the pH testing component has a sensor spot or a needle-type microsensor (PreSens GmbH, Regensburg, Germany). The sensor may be located between the two substrates and extend into component 1106 to facilitate measurement of the sample.

Components 1108 and 1110 represent additional testing components or reservoirs. The sample is routed to these components through pathways 1105b and 1105c. These testing components may be configured to conduct various QC tests as described herein. For example, the components 1108 and 1110 may be used for K222 testing, dissolved and gaseous $O_2$ levels, dissolved and gaseous $CO_2$ levels, and/or LAL testing. Each reservoir for the components 1108 and 1110 may be loaded or pre-loaded with any necessary reagent to mix with the sample and an outside detector (e.g., from the QC system) is able to interrogate the components 1108 and 1110 so as to measure and collect the return signal indicating the desired parameter being measured. It should be appreciated that other tests may be included in various combinations. The components 1108 and 1110 may be combination testing components performing more than one QC test each.

Component 1112 represents a HPLC system. The HPLC component 1112 includes an inlet 1114. The present invention contemplates that the inlet 1114 may be fluidically isolated from the inlet 1104 or it may be in direct fluid communication therewith. For example, this inlet may separated from the inlet 1104 with a fluid pathway 1115a. An optional valve 1117 may be present to facilitate fluid input and routing either through the HPLC component through the pathway 1115b or directly to the waste reservoir through the pathway 1115c. The component 1112 may be fluidly coupled through the pathway 1105d to the sample reservoir 1104. The HPLC component 1112 includes a separation column 1116 (e.g., a reverse phase column) and a detector cell 1118 (e.g., a diode-array detector). It should be appreciated that these components may be miniaturized to fit onto the cassette 1102. Upon exiting the detector cell 1118, the sample may proceed along pathway 1115d, which merges into pathway 1115c as shown.

The cassette 1102 includes a waste reservoir 1120 in fluid communication with components 1104, 1106, 1108, 1110, and 1112. Each of the testing components present on the cassette 1102 may be coupled to the waste reservoir 1120 through pathways 1107a-c and 1115c. The waste component 1120 may serve as a collection point for the fluid volume of the sample following the QC tests.

FIGS. 12A-C depict a pH measurement cell 1202 according to an exemplary embodiment of the invention. The cell 1202 is a pH measurement cell that may be used in a cassette for QC testing. For example, the cell 1202 may be used with the cassettes as described herein, such as FIG. 2, FIG. 5, and FIG. 11. FIG. 12A is a top view of the pH measurement cell, FIG. 12B is a cross-sectional view of the pH measurement cell, and FIG. 12C depicts an optical interface to a UV-Vis spectrophotometer.

The cell 1202 includes a sample inlet 1204 and a sample outlet 1206 and an elongate flow path 1205 extending in open fluid communication therebetween. As can be seen in FIG. 12, arrows indicate the sample flow path between the inlet 1204 and the outlet 1206. The cell 1202 includes spaced apart and opposed windows 1208a and 1208b in opposed overlying registry with a sample compartment 1210 (providing a widened section of the flow path 1205'). The windows 1208a and 1208b may be configured in different ways. According to some embodiments, the windows 1208a and 1208b may be a window with pH sensitive dye for spectroscopic pH measurement. Alternatively, the windows 1208a and 1208b may be a transparent spectroscopic grade window. Similarly, the sample compartment 1210 may have different configurations. According to some embodiments, the sample compartment 1210 may be empty. Alternatively, the sample compartment 1210 can be filled with pH sensitive gel. For example, the pH sensitive gel may be as described in Zaggout, et al., *Materials Letters*, 59: 2928-2931 (2005).

In FIG. 12C, a UV-Vis spectrophotometer light source 1212 is shown. Opposite the light source 1212 is a UV-Vis spectrophotometer detector 1214 as shown. The light source 1212 generates light waves 1216 which pass through the windows 1208a and 1208b and the sample in the sample compartment 1210. This provides one manner in which pH testing may be accomplished.

FIG. 13 depicts an alternative pH measurement cell 1302 according to an exemplary embodiment of the invention. This an alternative pH measurement cell 1302 is used when a longer light pathway is required to obtain sufficient sensitivity for the pH measurement. The cell 1302 may be a pH measurement cell that may be used in a cassette for QC testing. For example, the cell 1302 may be used with the cassettes as described herein, such as FIG. 2, FIG. 5, and FIG. 11. FIG. 13A is a top view of the pH measurement cell, FIG. 13B is a side view of the pH measurement cell, and FIG. 13C depicts an optical interface with a UV-Vis spectrophotometer.

In order to provide a longer light pathway, the cell 1302 uses a light pathway that is across the length or width of the cassette. The boundaries of the cell shown in FIG. 13A may represent the sides of a cassette. This is in contrast to the pH cell shown in FIG. 12 wherein the light pathway is across the thickness or height of a cassette. By using a longer pathway as described, increased sensitivity is obtained for poor light absorbing samples. Accordingly, the pathway depends upon the absorbance characteristics of the sample.

The cell 1302 has a sample inlet 1304 and a sample outlet 1306 and an elongate fluid path 1305 extending in fluid communication therebetween. As can be seen in FIG. 13, arrows indicate the sample flow path between the inlet 1304 and the outlet 1306. The cell 1302 includes a sample compartment 1310 spanning between windows 1308a and 1308b. The windows 1308a and 1308b may be configured in different ways. According to some embodiments, the windows 1308a and 1308b may be transparent spectroscopic grade windows. Similarly, the sample compartment 1310 can have different configurations. According to some embodiments, the sample compartment 1310 may be empty. Alternatively, the sample compartment 1310 may be filled with pH sensitive gel.

In FIG. 13C, a UV-Vis spectrophotometer light source 1312 is shown. Opposite the light source 1312 is a UV-Vis spectrophotometer detector 1314 as shown. The light source 1312 generates light waves 1316 which pass through the windows 1308a and 1308b and the sample. This provides one manner in which pH testing may be accomplished.

Figure 14B:
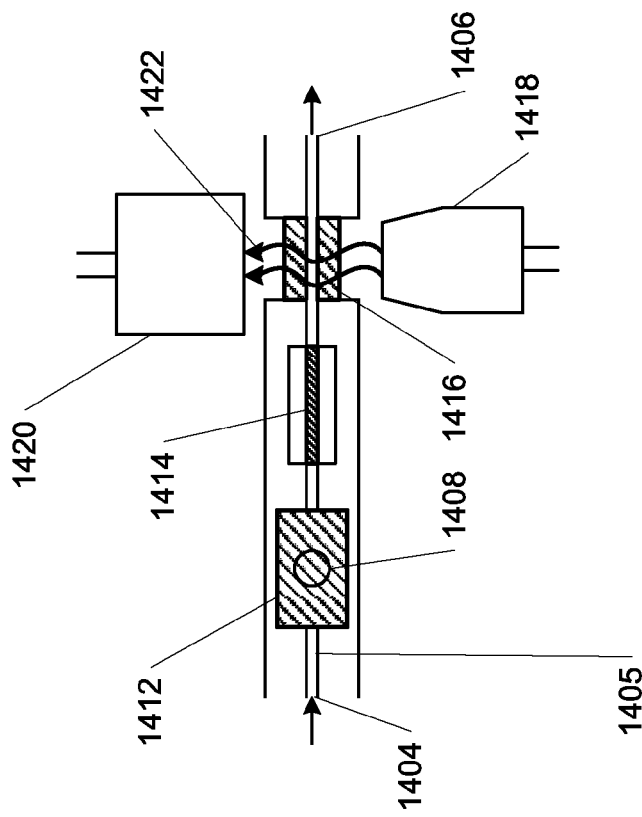
FIGS. 14A and 14B depict a miniaturized HPLC according to an exemplary embodiment.
Figure 14A:
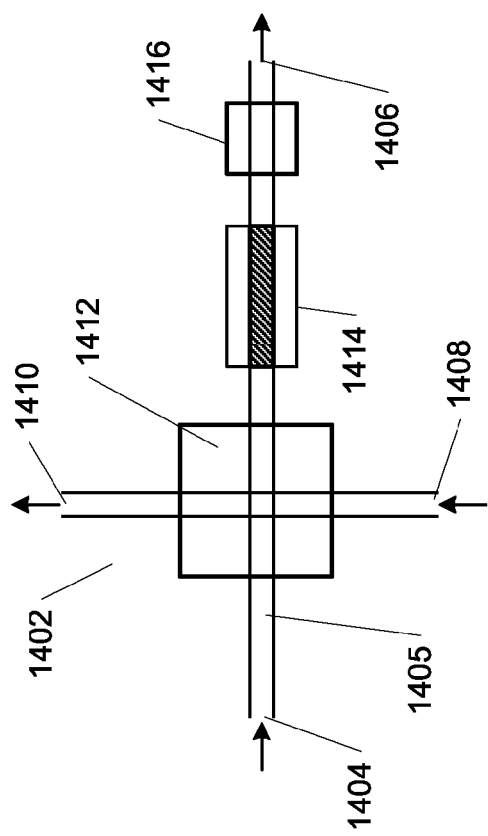

FIGS. 14A-B depict a miniaturized HPLC 1402 according to an exemplary embodiment of the invention. The miniaturized HPLC 1402 may be used in a cassette for QC testing. For example, the miniaturized HPLC may be used with the cassettes as described herein, such as FIG. 11. FIG. 14A is a top view of the miniaturized HPLC and FIG. 14B depicts a side view with an optical interface to a UV-Vis spectrophotometer.

The miniaturized HPLC 1402 has a sample inlet 1404 and a sample outlet 1406 and an elongate fluid path 1405 extending in fluid communication therebetween. As can be seen in FIG. 14, arrows indicate the sample flow path between the inlet 1404 and the outlet 1406. The miniaturized HPLC 1402 has a mobile phase inlet 1408 and a mobile phase by-pass outlet 1410.

A pulse generator 1412 is included. The pulse generator 1412 contains fluid path valves. A separation column 1414 is filled with sorbent material. Finally a UV/Vis detection cell 1416 is included.

In FIG. 14B, a UV-Vis spectrophotometer light source 1418 is shown. Opposite the light source 1418 is a UV-Vis spectrophotometer detector 1420 as shown. The light source 1418 generates light waves 1422 which pass through the sample as shown.

The miniaturized HPLC 1402 may be able to separate, detect, and calculate results within an exemplary timeframe of 10 to 15 minutes. It should be appreciated that alternatives to this structure may be used such as a UV/Vis fluorescence detector or a gamma ray detector. The miniaturized HPLC 1402 may be able to be fit onto a cassette as shown and described herein. In some embodiments, certain parts of the HPLC may be located on a cassette and certain located off the cassette, such as in the QC system. For example, the pulse generator, the light source, and the detector may be located in the QC system.

While the foregoing description includes details and specific examples, it is to be understood that these have been included for purposes of explanation only, and are not to be interpreted as limitations of the present invention.

While the embodiments have been particularly shown and described above, it will be appreciated that variations and modifications may be effected by a person of ordinary skill in the art without departing from the scope of the invention. Furthermore, one of ordinary skill in the art will recognize that such processes and systems do not need to be restricted to the specific embodiments described herein. Other embodiments, combinations of the present embodiments, and uses and advantages of the present invention will be apparent to those skilled in the art from consideration of the specification and practice of the invention disclosed herein. The specification and examples should be considered exemplary.

What is claimed is:

1. An analysis system comprising:
   a port configured to operatively receive and engage a cassette comprising one or more analysis components, wherein the cassette is being introduced with one or more reference samples;
   a head-space mass spectrometer that determines the presence of residual solvents in the system; and
   one or more sub-systems comprising one or more computer processors configured to interface with the one or more analysis components causing the one or more analysis components to conduct analysis of a signal from a sample of a radiopharmaceutical contained in the cassette and simultaneously calibrate the signal from the sample based on a comparison between the sample and the one or more reference samples,
   collect analyzed data from the analysis components, and
   provide an output of one or more results based upon the analyzed data.

2. The system of claim 1, further comprising:
   a shield, substantially surrounding the cassette when received in the port, that reduces the escape of radiation from the system.

3. The system of claim 1, wherein the cassette is a disposable cassette.

4. The system of claim 1, wherein the cassette comprises one or more analysis components in a lab on a chip format.

5. The system of claim 1, the one or more analysis components comprising one or more of the following: a pH analysis component; a chemical purity analysis component; a radiochemical purity analysis component; a radionuclidic purity analysis component or an appearance analysis component.

6. The system of claim 1, the one or more analysis components comprising a high pressure liquid chromatograph, a capillary electrophoresis unit, a K222 test, or a limulus amebocyte lysate test.

7. The system of claim 1, further comprising:
   a radiopharmaceutical manufacturing system integrated with the analysis system.

8. The system of claim 1, further comprising:
   a radiopharmaceutical dispensing system integrated with the analysis system comprising a manifold sub-system that fluidly couples the analysis system to the radiopharmaceutical dispensing system.

9. The system of claim 1, wherein the cassette is configured for testing a particular radiopharmaceutical for use in conjunction with conducting a SPECT or a PET scan.

10. An analysis system comprising:
an enclosed, disposable fluid path within a disposable cassette including one or more reference samples;
a port configured to operatively receive and engage the cassette; and
one or more sub-systems comprising one or more computer processors configured to interface with one or more analysis components that interact with the disposable fluid path causing the one or more analysis components to conduct analysis of a signal from a sample, contained entirely within the fluid path and simultaneously calibrate the signal from the sample based on a comparison between the sample and the one or more reference samples, collect analyzed data from the analysis components, and provide an output of one or more results based upon the analyzed data; and
at least one of the one or more analysis components comprises a head-space mass spectrometer that determines the presence of residual solvents in the system.

11. The system of claim 10, the disposable cassette comprising a microfluidic device comprising an intake reservoir and a waste reservoir.

12. The system of claim 10, further comprising:
a shield, substantially surrounding the cassette, that substantially reduces the escape of radiation from the system.

13. The system of claim 10, wherein the cassette comprises one or more analysis components in a lab on a chip format.

14. The system of claim 10, the one or more analysis components comprising one or more of the following: a pH analysis component; a chemical purity analysis component; a radiochemical purity analysis component; a radionuclidic purity analysis component or an appearance analysis component.

15. The system of claim 10, the one or more analysis components comprising a high pressure liquid chromatograph, a capillary electrophoresis unit, a K222 test, or a limulus amebocyte lysate test.

16. The system of claim 10, further comprising:
a radiopharmaceutical manufacturing system integrated with the analysis system.

17. The system of claim 10, further comprising:
a radiopharmaceutical dispensing system integrated with the analysis system comprising a manifold sub-system that fluidly couples the analysis system to the radiopharmaceutical dispensing system.

18. The system of claim 10, wherein the sample comprises a radiopharmaceutical for use in conjunction with conducting a SPECT or a PET scan.

19. A cassette comprising:
an intake reservoir for receiving a volume of a sample of a radiopharmaceutical;
analysis components comprising a pH test, a limulus amebocyte lysate test, a radiochemical purity analysis test, a K222 test, and a visual appearance test, wherein the analysis components further include one or more reference locations containing one or more reference samples;
fluidic flow paths fluidically coupling the intake reservoir and each of the analysis components;
the cassette further being disposable and configured to operatively interface with an external system that enables conduct of at least the radiochemical purity test based on analysis of a signal from the sample of the radiopharmaceutical and simultaneously calibrate the signal from the sample based on a comparison between the sample and the one or more reference samples.

20. A method comprising:
accepting an input of a sample of a radiopharmaceutical, wherein the sample is accepted through an intake reservoir of a disposable cassette;
causing the sample to be fluidically distributed along one or more fluidic pathways to a sample input location located at each of a plurality of analysis components located on the disposable cassette, wherein the analysis components comprise: a pH test, a limulus amebocyte lysate test, a radiochemical purity analysis test, a K222 test, and a visual appearance test, wherein further the fluid distribution initiates the performance of the tests;
impinging the sample located at each of the plurality of analysis components with one or more signals from one or more signal sources located external to the disposable cassette;
analyzing a signal from the sample of the radiopharmaceutical and simultaneously calibrating the signal from the sample based on a comparison between the sample and one or more reference samples; and
observing the results of the tests on the disposable cassette wherein the results of the pH test, the limulus amebocyte lysate test, the radiochemical purity analysis test, and the K222 test are determined through comparison to the one or more reference samples.

* * * * *